US012799196B2

(12) United States Patent
Du et al.

(10) Patent No.: US 12,799,196 B2
(45) Date of Patent: Nov. 17, 2026

(54) ANTI-CLDN6 ANTIBODY AND USE THEREOF

(71) Applicant: SHANGHAI GENBASE BIOTECHNOLOGY CO., LTD., Shanghai (CN)

(72) Inventors: Liang Du, Shanghai (CN); Hongyan Zhang, Shanghai (CN); Lina Jin, Shanghai (CN); Yali Chen, Shanghai (CN); Tingting Wan, Shanghai (CN); Liuliu Xu, Shanghai (CN); Jijun Yuan, Shanghai (CN)

(73) Assignee: SHANGHAI GENBASE BIOTECHNOLOGY CO., LTD., Shanghai (CN)

( * ) Notice: Subject to any disclaimer, the term of this patent is extended or adjusted under 35 U.S.C. 154(b) by 562 days.

(21) Appl. No.: 18/280,379

(22) PCT Filed: Mar. 5, 2021

(86) PCT No.: PCT/CN2021/079380
§ 371 (c)(1),
(2) Date: Sep. 5, 2023

(87) PCT Pub. No.: WO2022/183502
PCT Pub. Date: Sep. 9, 2022

(65) Prior Publication Data

US 2024/0150455 A1 May 9, 2024

(51) Int. Cl.

| | |
|---|---|
| ***C07K 16/28*** | (2006.01) |
| ***A61K 39/395*** | (2006.01) |
| ***A61K 40/11*** | (2025.01) |
| ***A61K 40/15*** | (2025.01) |
| ***A61K 40/31*** | (2025.01) |
| ***A61K 40/42*** | (2025.01) |
| ***A61K 45/06*** | (2006.01) |
| ***A61K 47/68*** | (2017.01) |
| ***A61P 35/00*** | (2006.01) |
| ***G01N 33/575*** | (2026.01) |

(52) U.S. Cl.
CPC .......... *C07K 16/28* (2013.01); *A61K 39/3955* (2013.01); *A61K 40/11* (2025.01); *A61K 40/15* (2025.01); *A61K 40/31* (2025.01); *A61K 40/4202* (2025.01); *A61K 45/06* (2013.01); *A61K 47/6849* (2017.08); *A61P 35/00* (2018.01); *G01N 33/5759* (2026.01); *C07K 2317/24* (2013.01); *C07K 2317/31* (2013.01); *C07K 2317/622* (2013.01)

(58) Field of Classification Search
CPC ................ A61K 40/31; A61K 47/6849; A61K 2039/505
See application file for complete search history.

(56) References Cited

U.S. PATENT DOCUMENTS

2011/0059469 A1 3/2011 Aburatani et al.

FOREIGN PATENT DOCUMENTS

| | | | |
|---|---|---|---|
| CN | 101918450 | A | 12/2010 |
| CN | 105813650 | A | 7/2016 |
| CN | 106432500 | A | 2/2017 |
| CN | 107207580 | A | 9/2017 |
| CN | 111875703 | A | 11/2020 |
| EP | 2241578 | A1 | 10/2010 |
| JP | 2013-510808 | A | 3/2013 |
| JP | 2016-536020 | A | 11/2016 |
| WO | 2009/087978 | A1 | 5/2011 |
| WO | WO 2011057788 | | 5/2011 |
| WO | WO 2015069794 | | 5/2015 |
| WO | WO 2016073649 | | 5/2016 |
| WO | 2020/191344 | A1 | 9/2020 |
| WO | WO2020191342 | A | 9/2020 |

OTHER PUBLICATIONS

Almagro et. al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Marvin et. al., Biochemistry, 42(23):7077-7083 (2003) (Year: 2003).*
Chiu et al., Antibodies, 8(55):1-80. (2019) (Year: 2019).*
Stedman's Medical dictionary, 2012, p. 11760, (Year: 2012).*
Kojima et al., "Prognostic Significance of Aberrant Claudin-6 Expression in Endometrial Cancer," Cancers, 12:2748 (2021).

* cited by examiner

*Primary Examiner* — Julie Wu
*Assistant Examiner* — Francesca Edgingtongiordano
(74) *Attorney, Agent, or Firm* — Leason Ellis LLP; James F. Haley, Jr.; Kendra V. Johnson

(57) ABSTRACT

Provided are an anti-CLDN6 antibody or an antigen-binding fragment thereof; a nucleic acid molecule encoding same; an immunoconjugate, a bispecific molecule, a chimeric antigen receptor and a pharmaceutical composition containing same; and the use thereof for preventing and/or treating tumors.

24 Claims, 4 Drawing Sheets

Specification includes a Sequence Listing.

ANTI-CLDN6 ANTIBODY AND USE THEREOF

CROSS-REFERENCE TO RELATED APPLICATIONS

This application is a United States National Phase Application filed under 35 U.S.C. § 371 from International Patent Application No. PCT/CN2021/079380, filed on Mar. 5, 2021. The content and disclosure of the foregoing application are incorporated by reference herein in its entirety.

SEQUENCE LISTING

The instant application contains a Sequence Listing which is submitted electronically in text format in lieu of a paper copy and is hereby incorporated by reference in its entirety. Said text copy, created on Sep. 1, 2023, is named 000362-0007-301_Sequence.txt and is 20,814 bytes in size. The text file is being submitted electronically via EFS-Web.

TECHNICAL FIELD

The present invention relates to the fields of disease treatment and immunology. Specifically, the present invention relates to an anti-CLDN6 antibody or antigen-binding fragment thereof, a nucleic acid molecule encoding the same, an immunoconjugate, bispecific molecule, chimeric antigen receptor and pharmaceutical composition comprising the same, and use thereof for preventing and/or treating a tumor.

BACKGROUND

Ovarian cancer (OC) is a common gynecological malignancy, which is a highly heterogeneous epithelial tumor with different histological subtypes and genetic and biological characteristics, including serous carcinoma, endometrioid carcinoma, clear-cell carcinoma and mucinous carcinoma. Globally, there are 310,000 new cases of ovarian cancer and more than 200,000 deaths each year. About 75% of ovarian cancers are of serous carcinoma, which has a five-year survival rate of 35%, is a type of cancer with strong malignancy and is usually diagnosed at an advanced stage. This type of tumor exhibits extraordinary aggressiveness. In terms of targeted drugs, in addition to anti-angiogenic therapy that has been clinically proven to improve the progression-free survival of patients with serous ovarian cancer at stages III to IV, advanced serous ovarian cancer is initially responsive to platinum-based chemotherapy, but relapses shortly after initial response, and primary treatment is surgery in approximately 70% to 80% of cases. In recent years, studies on the pathogenesis and molecular characteristics of ovarian cancer have provided more scientific basis and insights for targeted therapy of ovarian cancer. About 90% of ovarian cancers are associated with spontaneous somatic mutations of TP53, and more importantly, BRCA1 and BRCA2 mutations, which lead to genetic instability and homozygous defects in homologous DNA repair that are the main causes of malignant transformation of cells. These studies provide a basis for treating ovarian cancer with a drug targeting poly ADP-ribose polymerase (PARP), but its actual effect has yet to be clinically proven.

Claudin (CLDN) is a transmembrane protein that is a membrane protein located at the tight junction of epithelial cells and endothelial cells. The distribution of CLDN family proteins is specific to tissues and organs, and their main functions are intercellular adhesion, maintaining cell polarity, regulating paracellular permeability, and participating in the regulation of cell proliferation and differentiation. Recent studies have shown that some members of the CLDN family are up-regulated in the process of carcinogenesis, and are ectopically activated during the carcinogenesis in tissues in which they are non-normally distributed, and this feature has led scientists to further consider the possibility of CLDN protein as a tumor target. In 2016, the American Society of Clinical Oncology (ASCO) reported the phase II clinical study of zolbetuimab, a monoclonal antibody drug targeting CLDN18.2, and zolbetuimab combined with chemotherapeutics significantly increased the overall survival and progression-free survival, the drug is currently undergoing phase III clinical trials for gastric cancer and phase II clinical trials for pancreatic cancer. The success of drugs targeting CLDN18.2 has further enhanced scientists' confidence in CLDN family members as tumor targets.

A large number of research data in TCGA show that the level of CLDN6 in ovarian cancer patients is significantly up-regulated compared with normal ovarian tissue. The level of CLDN6 in normal ovarian tissue is 0 TPM (transcripts per million, n=88), while the level of CLDN6 in ovarian tumor is 31.4 TPM (n=426). In addition, CLDN6 is highly expressed only during embryonic development, and is not expressed in normal adult tissues. Among normal adult tissues, testis shows the highest expression of CLDN6, and the expression level is only 0.83 TPM. In addition to the high expression in ovarian cancer, CLDN6 is also highly expressed in testicular cancer (159.9 TPM, n=137), uterine sarcoma (8.4 TPM, n=57), and some endometrial cancers, gastric cancers, and lung cancers. Studies have shown that the high expression of CLDN6 in endometrial cancer is associated with multiple clinicopathological factors and is an independent prognostic factor. Kaplan-Meier analysis showed that there were significant differences in the overall survival rate and recurrence-free survival rate between the CLDN6 high expression group and the low expression group, the 5-year survival rate of the high CLDN6 expression group was about 30%, while the 5-year survival rate of the low expression group was 89%. In addition to endometrial cancer, the high expression of CLDN6 is also negatively correlated with the prognosis of gastric cancer and urothelial cancer. Non-expression in normal tissues, high expression in tumor tissues, and negative correlation with tumor prognosis make CLDN6 an ideal tumor target.

CLDN6 protein is a quadruple transmembrane protein that has four transmembrane hydrophobic regions and two extracellular loops. It is extremely difficult to express its recombinant protein, so there is no suitable protein antigen for immunization, which brings difficulties to the immunization and screening of antibodies against CLDN6. In addition, the CLDN family proteins have high homology. When targeting CLDN6, it is necessary to avoid binding with CLDN3 and CLDN4, which are widely expressed in normal tissues and have high homology with CLDN6, so as to avoid possible cross-binding that may lead to toxicity issues. The above are two major difficulties in the development of anti-CLDN6 antibodies.

CLDN9 is the protein with the highest homology to CLDN6 in the CLDN family. TCGA data show that CLDN9 is lowly expressed in pancreas (4.23 TPM, n=4), lowly expressed in kidney (1.99 TPM, n=25), and barely expressed in other normal tissues (the highest expression level is found in bile duct, that is 0.82 TPM, n=9). At the same time, CLDN9 is up-regulated in ovarian cancer (5.68 TPM, n=426), and up-regulated in cholangiocarcinoma (8.44 TPM, n=36).

Therefore, it is urgent and necessary to develop an anti-CLDN6 antibody and an anti-CLDN6 and/or anti-CLDN9 antibody with higher specificity and lower toxic and side effects, which will give cancer patients more drug options.

Contents of the Invention

The antibody of the present invention can specifically recognize/bind to human CLDN6 and/or CLDN9, and can induce killing of a cell expressing CLDN6 (e.g., a tumor cell) through ADCC and/or CDC. Therefore, the antibody of the present invention has a potential to be used for prevention and/or treatment of a tumor, and thus has great clinical value.

Antibody of the Present Invention

Therefore, in one aspect, the present invention provides an antibody or antigen-binding fragment thereof capable of specifically binding to CLDN6, and the antibody or antigen-binding fragment thereof comprises:

(a) a heavy chain variable region (VH) comprising the following 3 complementarity determining regions (CDRs):

(i) a VH CDR1, which consists of the following sequence: SEQ ID NO: 3, or a sequence having a substitution, deletion or addition of one or several amino acids (e.g., a substitution, deletion or addition of 1, 2 or 3 amino acids) as compared thereto, (ii) a VH CDR2, which consists of the following sequence: SEQ ID NO: 4 or 33, or a sequence having a substitution, deletion or addition of one or several amino acids (e.g., a substitution, deletion or addition of 1, 2 or 3 amino acids) as compared thereto, and (iii) a VH CDR3, which consists of the following sequence: SEQ ID NO: 5, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):

(iv) a VL CDR1, which consists of the following sequence: SEQ ID NO: 6, or a sequence having a substitution, deletion or addition of one or several amino acids (e.g., a substitution, deletion or addition of 1, 2 or 3 amino acids) as compared thereto, (v) a VL CDR2, which consists of the following sequence: SEQ ID NO: 7, or a sequence having a substitution, deletion or addition of one or several amino acids (e.g., a substitution, deletion or addition of 1, 2 or 3 amino acids) as compared thereto, and (vi) a VL CDR3, which consists of the following sequence: SEQ ID NO: 8, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In some preferred embodiments, the antibody or antigen-binding fragment thereof comprises: the following 3 heavy chain CDRs: VH CDR1 having the sequence as set forth in SEQ ID NO: 3, VH CDR2 having the sequence as set forth in SEQ ID NO: 4, and VH CDR3 having the sequence as set forth in SEQ ID NO: 5; and/or, the following 3 light chain CDRs: VL CDR1 having the sequence as set forth in SEQ ID NO: 6, VL CDR2 having the sequence as set forth in SEQ ID NO: 7, and VL CDR3 having the sequence as set forth in SEQ ID NO: 8.

In some preferred embodiments, the antibody or antigen-binding fragment thereof comprises: the following 3 heavy chain CDRs: VH CDR1 having the sequence as set forth in SEQ ID NO: 3, VH CDR2 having the sequence as set forth in SEQ ID NO: 33, and VH CDR3 having the sequence as set forth in SEQ ID NO: 5; and/or, the following 3 light chain CDRs: VL CDR1 having the sequence as set forth in SEQ ID NO: 6, VL CDR2 having the sequence as set forth in SEQ ID NO: 7, and VL CDR3 having the sequence as set forth in SEQ ID NO: 8.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In certain preferred embodiments, the present invention provides an antibody or antigen-binding fragment thereof capable of specifically binding to CLDN6, and the antibody or antigen-binding fragment thereof comprises:

(a) a heavy chain variable region (VH) comprising the following 3 complementarity determining regions (CDRs):

(i) a VH CDR1, which consists of the following sequence: SEQ ID NO: 3, or a sequence having a substitution, deletion or addition of one or several amino acids (e.g., a substitution, deletion or addition of 1, 2 or 3 amino acids) as compared thereto, (ii) a VH CDR2, which consists of the following sequence: SEQ ID NO: 4, or a sequence having a substitution, deletion or addition of one or several amino acids (e.g., a substitution, deletion or addition of 1, 2 or 3 amino acids) as compared thereto, and (iii) a VH CDR3, which consists of the following sequence: SEQ ID NO: 5, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):

(iv) a VL CDR1, which consists of the following sequence: SEQ ID NO: 6, or a sequence having a substitution, deletion or addition of one or several amino acids (e.g., a substitution, deletion or addition of 1, 2 or 3 amino acids) as compared thereto, (v) a VL CDR2, which consists of the following sequence: SEQ ID NO: 7, or a sequence having a substitution, deletion or addition of one or several amino acids (e.g., a substitution, deletion or addition of 1, 2 or 3 amino acids) as compared thereto, and (vi) a VL CDR3, which consists of the following sequence: SEQ ID NO: 8, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In some preferred embodiments, the antibody or antigen-binding fragment thereof comprises: the following 3 heavy chain CDRs: VH CDR1 having the sequence as set forth in SEQ ID NO: 3, VH CDR2 having the sequence as set forth in SEQ ID NO: 4, and VH CDR3 having the sequence as set forth in SEQ ID NO: 5; and/or, the following 3 light chain CDRs: VL CDR1 having the sequence as set forth in SEQ ID NO: 6, VL CDR2 having the sequence as set forth in SEQ ID NO: 7, and VL CDR3 having the sequence as set forth in SEQ ID NO: 8.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In some preferred embodiments, the antibody or antigen-binding fragment thereof has one or more of the following biological functions:

(a) binding to human CLDN6 with an EC50 of 5 μg/ml or less (e.g., 3 μg/ml or less);
(b) not binding to human CLDN3, CLDN4 and CLDN9;
(c) inducing killing of a cell expressing human CLDN6 (e.g., a tumor cell, such as a tumor cell expressing CLDN6) through antibody-dependent cell-mediated cytotoxicity (ADCC);
(d) inducing killing of a cell expressing human CLDN6 (e.g., a tumor cell, such as a tumor cell expressing CLDN6) through complement-dependent cytotoxicity (CDC);
(e) preventing and/or treating a tumor (e.g., a CLDN6-expressing tumor) in a subject.

In an exemplary embodiment, the antibody or antigen-binding fragment thereof comprises:

(a) a heavy chain variable region (VH) comprising an amino acid sequence selected from the group consisting of:
(i) the sequence as set forth in SEQ ID NO: 1;
(ii) a sequence having a substitution, deletion or addition of one or several amino acids (e.g., a substitution, deletion or addition of 1, 2, 3, 4 or 5 amino acids) as compared with the sequence as set forth in SEQ ID NO: 1; or
(iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 1;

and/or, (b) a light chain variable region (VL) comprising an amino acid sequence selected from the group consisting of:
(iv) the sequence as set forth in SEQ ID NO: 2;
(v) a sequence having a substitution, deletion or addition of one or several amino acids (e.g., a substitution, deletion or addition of 1, 2, 3, 4 or 5 amino acids) as compared with the sequence as set forth in SEQ ID NO: 2; or
(vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 2.

In certain preferred embodiments, the substitution described in (ii) or (v) is a conservative substitution.

In certain preferred embodiments, the antibody or antigen-binding fragment thereof comprises: a VH having the sequence as set forth in SEQ ID NO: 1 and a VL having the sequence as set forth in SEQ ID NO: 2.

In certain preferred embodiments, the present invention provides an antibody or antigen-binding fragment thereof capable of specifically binding to CLDN6, and the antibody or antigen-binding fragment thereof comprises:

(a) a heavy chain variable region (VH) comprising the following 3 complementarity determining regions (CDRs):
(i) a VH CDR1, which consists of the following sequence: SEQ ID NO: 3, or a sequence having a substitution, deletion or addition of one or several amino acids (e.g., a substitution, deletion or addition of 1, 2 or 3 amino acids) as compared thereto,
(ii) a VH CDR2, which consists of the following sequence: SEQ ID NO: 33, or a sequence having a substitution, deletion or addition of one or several amino acids (e.g., a substitution, deletion or addition of 1, 2 or 3 amino acids) as compared thereto, and
(iii) a VH CDR3, which consists of the following sequence: SEQ ID NO: 5, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):
(iv) a VL CDR1, which consists of the following sequence: SEQ ID NO: 6, or a sequence having a substitution, deletion or addition of one or several amino acids (e.g., a substitution, deletion or addition of 1, 2 or 3 amino acids) as compared thereto,
(v) a VL CDR2, which consists of the following sequence: SEQ ID NO: 7, or a sequence having a substitution, deletion or addition of one or several amino acids (e.g., a substitution, deletion or addition of 1, 2 or 3 amino acids) as compared thereto, and
(vi) a VL CDR3, which consists of the following sequence: SEQ ID NO: 8, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In certain preferred embodiments, the antibody or antigen-binding fragment thereof comprises: the following 3 heavy chain CDRs: VH CDR1 having the sequence as set forth in SEQ ID NO: 3, VH CDR2 having the sequence as set forth in SEQ ID NO: 33, and VH CDR3 having the sequence as set forth in SEQ ID NO: 5; and/or, the following 3 light chain CDRs: VL CDR1 having the sequence as set forth in SEQ ID NO: 6, VL CDR2 having the sequence as set forth in SEQ ID NO: 7, and VL CDR3 having the sequence as set forth in SEQ ID NO: 8.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In an exemplary embodiment, the antibody or antigen-binding fragment thereof comprises:

(a) a heavy chain variable region (VH) comprising an amino acid sequence selected from the group consisting of:

(i) the sequence as set forth in SEQ ID NO: 19;

(ii) a sequence having a substitution, deletion or addition of one or several amino acids (e.g., a substitution, deletion or addition of 1, 2, 3, 4 or 5 amino acids) as compared with the sequence as set forth in SEQ ID NO: 19; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 19;

and/or, (b) a light chain variable region (VL) comprising an amino acid sequence selected from the group consisting of:

(iv) the sequence as set forth in SEQ ID NO: 20;

(v) a sequence having a substitution, deletion or addition of one or several amino acids (e.g., a substitution, deletion or addition of 1, 2, 3, 4 or 5 amino acids) as compared with the sequence as set forth in SEQ ID NO: 20; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 20.

In certain preferred embodiments, the substitution described in (ii) or (v) is a conservative substitution.

In certain preferred embodiments, the antibody or antigen-binding fragment thereof comprises: a VH having the sequence as set forth in SEQ ID NO: 19 and a VL having the sequence as set forth in SEQ ID NO: 20.

In another aspect, the present invention provides an antibody or antigen-binding fragment thereof capable of specifically binding to CLDN6 and/or CLDN9, and the antibody or antigen-binding fragment thereof comprises:

(a) a heavy chain variable region (VH) comprising the following 3 complementarity determining regions (CDRs):

(i) a VH CDR1, which consists of the following sequence: SEQ ID NO: 13, or a sequence having a substitution, deletion or addition of one or several amino acids (e.g., a substitution, deletion or addition of 1, 2 or 3 amino acids) as compared thereto, (ii) a VH CDR2, which consists of the following sequence: SEQ ID NO: 14 or 23, or a sequence having a substitution, deletion or addition of one or several amino acids (e.g., a substitution, deletion or addition of 1, 2 or 3 amino acids) as compared thereto, and (iii) a VH CDR3, which consists of the following sequence: SEQ ID NO: 15, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):

(iv) a VL CDR1, which consists of the following sequence: SEQ ID NO: 16 or 24, or a sequence having a substitution, deletion or addition of one or several amino acids (e.g., a substitution, deletion or addition of 1, 2 or 3 amino acids) as compared thereto, (v) a VL CDR2, which consists of the following sequence: SEQ ID NO: 17, or a sequence having a substitution, deletion or addition of one or several amino acids (e.g., a substitution, deletion or addition of 1, 2 or 3 amino acids) as compared thereto, and (vi) a VL CDR3, which consists of the following sequence: SEQ ID NO: 18, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In certain preferred embodiments, the antibody or antigen-binding fragment thereof comprises: the following 3 heavy chain CDRs: VH CDR1 having the sequence as set forth in SEQ ID NO: 13, VH CDR2 having the sequence as set forth in SEQ ID NO: 14, and VH CDR3 having the sequence as set forth in SEQ ID NO: 15; and/or, the following 3 light chain CDRs: VL CDR1 having the sequence as set forth in SEQ ID NO: 16, VL CDR2 having the sequence as set forth in SEQ ID NO: 17, VL CDR3 having the sequence as set forth in SEQ ID NO: 18.

In certain preferred embodiments, the antibody or antigen-binding fragment thereof comprises: the following 3 heavy chain CDRs: VH CDR1 having the sequence as set forth in SEQ ID NO: 13, VH CDR2 having the sequence as set forth in SEQ ID NO: 23, and VH CDR3 having the sequence as set forth in SEQ ID NO: 15; and/or, the following 3 light chain CDRs: VL CDR1 having the sequence as set forth in SEQ ID NO: 24, VL CDR2 having the sequence as set forth in SEQ ID NO: 17, and VL CDR3 having the sequence as set forth in SEQ ID NO: 18.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In some preferred embodiments, the present invention provides an antibody or antigen-binding fragment thereof capable of specifically binding to CLDN6 and/or CLDN9, and the antibody or antigen-binding fragment thereof comprises:

(a) a heavy chain variable region (VH) comprising the following 3 complementarity determining regions (CDRs):

(i) a VH CDR1, which consists of the following sequence: SEQ ID NO: 13, or a sequence having a substitution, deletion or addition of one or several amino acids (e.g., a substitution, deletion or addition of 1, 2 or 3 amino acids) as compared thereto, (ii) a VH CDR2, which consists of the following sequence: SEQ ID NO: 14, or a sequence having a substitution, deletion or addition of one or several amino acids (e.g., a substitution, deletion or addition of 1, 2 or 3 amino acids) as compared thereto, and (iii) a VH CDR3, which consists of the following sequence: SEQ ID NO: 15, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):

(iv) a VL CDR1, which consists of the following sequence: SEQ ID NO: 16, or a sequence having a substitution, deletion or addition of one or several amino acids (e.g., a substitution, deletion or addition of 1, 2 or 3 amino acids) as compared thereto, (v) a VL CDR2, which consists of the following sequence: SEQ ID NO: 17, or a sequence having a substitution, deletion or addition of one or several amino acids (e.g., a substitution, deletion or addition of 1, 2 or 3 amino acids) as compared thereto, and (vi) a VL CDR3, which consists of the following sequence: SEQ ID NO: 18, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In certain preferred embodiments, the antibody or antigen-binding fragment thereof comprises: the following 3 heavy chain CDRs: VH CDR1 having the sequence as set forth in SEQ ID NO: 13, VH CDR2 having the sequence as set forth in SEQ ID NO: 14, and VH CDR3 having the sequence as set forth in SEQ ID NO: 15; and/or, the following 3 light chain CDRs: VL CDR1 having the sequence as set forth in SEQ ID NO: 16, VL CDR2 having the sequence as set forth in SEQ ID NO: 17, and VL CDR3 having the sequence as set forth in SEQ ID NO: 18.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In some preferred embodiments, the antibody or antigen-binding fragment thereof has one or more of the following biological functions:

(a) binding to human CLDN6 with an EC50 of 5 μg/ml or less (e.g., 3 μg/ml or less);

(b) not binding to human CLDN3 and CLDN4;

(c) inducing killing of a cell expressing human CLDN6 (e.g., a tumor cell, such as a tumor cell expressing CLDN6) through antibody-dependent cell-mediated cytotoxicity (ADCC);

(d) inducing killing of a cell expressing human CLDN6 (e.g. a tumor cell, such as a tumor cell expressing CLDN6) through complement-dependent cytotoxicity (CDC);

(e) preventing and/or treating a tumor (e.g., a CLDN6-expressing tumor) in a subject.

In an exemplary embodiment, the antibody or antigen-binding fragment thereof comprises:

(a) a heavy chain variable region (VH) comprising an amino acid sequence selected from the group consisting of:

(i) the sequence as set forth in SEQ ID NO: 11;

(ii) a sequence having a substitution, deletion or addition of one or several amino acids (e.g., a substitution, deletion or addition of 1, 2, 3, 4 or 5 amino acids) as compared with the sequence as set forth in SEQ ID NO: 11; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 11;

and/or, (b) a light chain variable region (VL) comprising an amino acid sequence selected from the group consisting of:

(iv) the sequence as set forth in SEQ ID NO: 12;

(v) a sequence having a substitution, deletion or addition of one or several amino acids (e.g., a substitution, deletion or addition of 1, 2, 3, 4 or 5 amino acids) as compared with the sequence as set forth in SEQ ID NO: 12; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 12.

In certain preferred embodiments, the substitution described in (ii) or (v) is a conservative substitution.

In certain preferred embodiments, the antibody or antigen-binding fragment thereof comprises: a VH having the sequence as set forth in SEQ ID NO: 11 and a VL having the sequence as set forth in SEQ ID NO: 12.

In some preferred embodiments, the present invention provides an antibody or antigen-binding fragment thereof capable of specifically binding to CLDN6 and/or CLDN9, and the antibody or antigen-binding fragment thereof comprises:

(a) a heavy chain variable region (VH) comprising the following 3 complementarity determining regions (CDRs):

(i) a VH CDR1, which consists of the following sequence: SEQ ID NO: 13, or a sequence having a substitution, deletion or addition of one or several amino acids (e.g., a substitution, deletion or addition of 1, 2 or 3 amino acids) as compared thereto, (ii) a VH CDR2, which consists of the following sequence: SEQ ID NO: 23, or a sequence having a substitution, deletion or addition of one or several amino acids (e.g., a substitution, deletion or addition of 1, 2 or 3 amino acids) as compared thereto, and (iii) a VH CDR3, which consists of the following sequence: SEQ ID NO: 15, or a sequence having a substitution, deletion or addition of one or several amino acids (e.g., a substitution, deletion or addition of 1, 2 or 3 amino acids) as compared thereto;

and/or (b) a light chain variable region (VL) comprising the following 3 complementarity determining regions (CDRs):

(iv) a VL CDR1, which consists of the following sequence: SEQ ID NO: 24, or a sequence having a substitution, deletion or addition of one or several amino acids (e.g., a substitution, deletion or addition of 1, 2 or 3 amino acids) as compared thereto, (v) a VL CDR2, which consists of the following sequence: SEQ ID NO: 17, or a sequence having a substitution, deletion or addition of one or several amino acids (e.g., a substitution, deletion or addition of 1, 2 or 3 amino acids) as compared thereto, and (vi) a VL CDR3, which consists of the following sequence: SEQ ID NO: 18, or a sequence having a substitution, deletion or addition of one or several amino acids (e.g., a substitution, deletion or addition of 1, 2 or 3 amino acids) as compared thereto.

In certain preferred embodiments, the substitution described in any one of (i) to (vi) is a conservative substitution.

In certain preferred embodiments, the CDRs described in any one of (i) to (vi) are defined according to the Kabat, IMGT or Chothia numbering system.

In certain preferred embodiments, the CDRs described in any one of (i) to (vi) are defined according to the IMGT numbering system.

In certain preferred embodiments, the antibody or antigen-binding fragment thereof comprises: the following 3 heavy chain CDRs: VH CDR1 having the sequence as set forth in SEQ ID NO: 13, VH CDR2 having the sequence as set forth in SEQ ID NO: 23, and VH CDR3 having the sequence as set forth in SEQ ID NO: 15; and/or, the following 3 light chain CDRs: VL CDR1 having the sequence as set forth in SEQ ID NO: 24, VL CDR2 having the sequence as set forth in SEQ ID NO: 17, and VL CDR3 having the sequence as set forth in SEQ ID NO: 18.

In certain preferred embodiments, the antibody or antigen-binding fragment thereof further comprises a human-derived framework region sequence (e.g., a FR sequence of a human immunoglobulin).

In certain preferred embodiments, the human immunoglobulin is selected from the group consisting of human rearranged antibody sequences or human germline antibody sequences.

In some preferred embodiments, the antibody or antigen-binding fragment thereof has one or more of the following biological functions:

(a) binding to human CLDN6 with an EC50 of 5 μg/ml or less (e.g., 3 μg/ml or less);

(b) not binding to human CLDN3 and CLDN4;

(c) inducing killing of a cell expressing human CLDN6 (e.g., a tumor cell, such as a tumor cell expressing CLDN6) through antibody-dependent cell-mediated cytotoxicity (ADCC);

(d) inducing killing of a cell expressing human CLDN6 (e.g. a tumor cell, such as a tumor cell expressing CLDN6) through complement-dependent cytotoxicity (CDC);

(e) preventing and/or treating a tumor (e.g., a CLDN6-expressing tumor) in a subject.

In an exemplary embodiment, the antibody or antigen-binding fragment thereof comprises:

(a) a heavy chain variable region (VH) comprising an amino acid sequence selected from the group consisting of:

(i) the sequence as set forth in SEQ ID NO: 9;

(ii) a sequence having a substitution, deletion or addition of one or several amino acids (e.g., a substitution, deletion or addition of 1, 2, 3, 4 or 5 amino acids) as compared with the sequence as set forth in SEQ ID NO: 9; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 9;

and/or, (b) a light chain variable region (VL) comprising an amino acid sequence selected from the group consisting of:

(iv) the sequence as set forth in SEQ ID NO: 10;

(v) a sequence having a substitution, deletion or addition of one or several amino acids (e.g., a substitution, deletion or addition of 1, 2, 3, 4 or 5 amino acids) as compared with the sequence as set forth in SEQ ID NO: 10; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence as set forth in SEQ ID NO: 10.

In certain preferred embodiments, the substitution described in (ii) or (v) is a conservative substitution.

In certain preferred embodiments, the antibody or antigen-binding fragment thereof comprises: a VH having the sequence as set forth in SEQ ID NO: 9 and a VL having the sequence as set forth in SEQ ID NO: 10.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from human immunoglobulin, and/or the VL of the antibody or antigen-binding fragment thereof comprises a light chain variable region (VL) framework region (FR) derived from human immunoglobulin. In such embodiments, the heavy chain variable region FR and/or the light chain variable region FR of the antibody or antigen-binding fragment thereof may comprise one or more non-human (e.g., murine)

amino acid residues. For example, the heavy chain framework region FR and/or the light chain framework region FR may comprise one or more amino acid backmutations in which there are corresponding murine amino acid residues.

In certain preferred embodiments, the antibody or antigen-binding fragment thereof further comprises:

(a) a heavy chain constant region (CH) of a human immunoglobulin or variant thereof, wherein the variant has a substitution, deletion or addition of one or more amino acids (e.g., a substitution, deletion or addition of up to 20, up to 15, up to 10, or up to 5 amino acids; for example, a substitution, deletion or addition of 1, 2, 3, 4 or 5 amino acids) as compared to the wild-type sequence from which it is derived; and (b) a light chain constant region (CL) of a human immunoglobulin or variant thereof, wherein the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared to the wild-type sequence from which it is derived.

In certain preferred embodiments, the heavy chain constant region is an IgG heavy chain constant region, such as an IgG1, IgG2, IgG3 or IgG4 heavy chain constant region.

In certain preferred embodiments, the antibody or antigen-binding fragment thereof comprises a heavy chain constant region (CH) as set forth in SEQ ID NO: 21.

In certain preferred embodiments, the light chain constant region is a κ or λ light chain constant region.

In certain preferred embodiments, the antibody or antigen-binding fragment thereof comprises a light chain constant region (CL) as set forth in SEQ ID NO: 22.

In certain preferred embodiments, the antigen-binding fragment is selected from the group consisting of Fab, Fab', $(Fab)_2$, Fv, disulfide-linked Fv, scFv, diabody and single domain antibody (sdAb); and/or, the antibody is a murine antibody, a chimeric antibody, a humanized antibody, a bispecific antibody or a multispecific antibody.

In the present invention, the antibody or antigen-binding fragment thereof of the present invention may comprise such a variant that differs from the antibody or antigen-binding fragment thereof from which it is derived only in a conservative substitution of one or more amino acids (e.g., a conservative substitution of up to 20, up to 15, up to 10, or up to 5 amino acids), has a sequence identity of at least 85%, at least 90%, at least 95%, at least 96%, at least 97%, at least 98%, at least 99%, or 100% as compared to the antibody or antigen-binding fragment thereof from which it is derived, and substantially retains the above-mentioned biological functions of the antibody or antigen-binding fragment thereof from which it is derived.

Preparation of Antibody

The antibody of the present invention can be prepared by various methods known in the art, for example, by genetic engineering and recombination techniques. For example, DNA molecules encoding the heavy and light chain genes of the antibody of the present invention are obtained by chemical synthesis or PCR amplification. The resulting DNA molecules are inserted into an expression vector and then transfected into a host cell. Then, the transfected host cell is cultured under suitable conditions, and expresses the antibody of the present invention.

The antigen-binding fragment of the present invention can be obtained by hydrolyzing an intact antibody molecule (see, Morimoto et al., J. Biochem. Biophys. Methods 24: 107-117 (1992), and Brennan et al., Science 229: 81 (1985)). Alternatively, these antigen-binding fragments can also be produced directly by recombinant host cells (reviewed in Hudson, Curr. Opin. Immunol. 11: 548-557 (1999); Little et al., Immunol. Today, 21: 364-370 (2000)). For example, Fab' fragments can be obtained directly from host cells; Fab' fragments can be chemically coupled to form $F(ab')_2$ fragments (Carter et al., Bio/Technology, 10: 163-167 (1992)). In addition, Fv, Fab or $F(ab')_2$ fragments can also be directly isolated from the culture medium of recombinant host cells. Other techniques for preparing these antigen-binding fragments are well known to those of ordinary skill in the art.

Accordingly, in another aspect, the present invention provides an isolated nucleic acid molecule, which comprises a nucleotide sequence encoding the antibody or antigen-binding fragment thereof of the present invention, or a heavy chain variable region and/or light chain variable region thereof. In certain preferred embodiments, the isolated nucleic acid molecule encodes the antibody or antigen-binding fragment thereof of the present invention, or a heavy chain variable region and/or light chain variable region thereof.

In another aspect, the present invention provides a vector (e.g., a cloning vector or an expression vector) comprising the isolated nucleic acid molecule of the present invention. In certain preferred embodiments, the vector of the present invention is, for example, a plasmid, a cosmid, a phage, and the like. In certain preferred embodiments, the vector is capable of expressing the antibody or antigen-binding fragment thereof of the present invention in a subject (e.g., a mammal, for example, a human).

In another aspect, the present invention provides a host cell comprising the isolated nucleic acid molecule of the present invention or the vector of the present invention. Such host cell includes, but is not limited to, prokaryotic cell such as *E. coli* cell, eukaryotic cell such as yeast cell, insect cell, plant cell, and animal cell (e.g, mammalian cell, such as mouse cell, human cell, etc.). In certain preferred embodiments, the host cell of the present invention is a mammalian cell, such as a CHO (e.g., CHO-K1, CHO-S, CHO DG44).

In another aspect, provided is a method for producing the antibody or antigen-binding fragment thereof of the present invention, which comprises culturing the host cell of the present invention under a condition that allows the expression of the antibody or antigen-binding fragment thereof, and recovering the antibody or antigen-binding fragment thereof from a culture of the cultured host cell.

Derivatized Antibody

The antibody or antigen-binding fragment thereof of the present invention can be derivatized, for example, linked to another molecule (e.g., another polypeptide or protein). Typically, derivatization (e.g., labeling) of the antibody or antigen-binding fragment thereof does not adversely affect its binding to CLDN6 and/or CLDN9, particularly human CLDN6 and/or human CLDN9. Accordingly, the antibody or antigen-binding fragment thereof of the present invention is also intended to include such derivatized forms. For example, the antibody or antigen-binding fragment thereof of the present invention can be functionally linked (by chemical coupling, genetic fusion, non-covalent linkage, or otherwise) to one or more other molecular moieties, such as another antibody (e.g., forming a bispecific antibody), detection reagent, pharmaceutical reagent, and/or protein or polypeptide capable of mediating the binding of the antibody or antigen-binding fragment thereof to another molecule (e.g., avidin or polyhistidine tag). In addition, the antibody or antigen-binding fragment thereof of the present invention may also be derivatized with a chemical group, such as polyethylene glycol (PEG), methyl or ethyl, or glycosyl.

These groups can be used to improve the biological properties of the antibody, such as increasing serum half-life.

Accordingly, in certain preferred embodiments, the antibody or antigen-binding fragment thereof of the present invention are labeled. In certain preferred embodiments, the antibody or antigen-binding fragment thereof of the present invention comprises a detectable label, such as enzyme, radionuclide, fluorescent dye, luminescent substance (e.g., chemiluminescent substance), or biotin. The detectable label of the present invention can be any substance detectable by fluorescent, spectroscopic, photochemical, biochemical, immunological, electrical, optical or chemical means. Such labels are well known in the art, examples of which include, but are not limited to, enzymes (e.g., horseradish peroxidase, alkaline phosphatase, β-galactosidase, urease, glucose oxidase, etc.), radionuclides (e.g., $^{3}H$, $^{125}I$, $^{35}S$, $^{14}C$, or $^{32}P$), fluorescent dyes (e.g., fluorescein isothiocyanate (FITC), fluorescein, tetramethylrhodamine isothiocyanate (TRITC), phycoerythrin (PE), Texas Red, rhodamine, quantum dots or cyanine dye derivatives (e.g., Cy7, Alexa 750)), luminescent substances (e.g., chemiluminescent substances, such as acridinium ester compounds), magnetic beads (e.g., Dynabeads®), calorimetric markers such as colloid gold or colored glass or plastic (e.g., polystyrene, polypropylene, latex, etc.) beads, and biotin for binding to the above-mentioned label-modified avidin (e.g., streptavidin). Patents that teach the use of such labels include, but are not limited to, U.S. Pat. Nos. 3,817,837; 3,850,752; 3,939,350; 3,996,345; 4,277,437; 4,275,149; and 4,366,241 (all of which are incorporated herein by reference in their entirety). The detectable labels as described above can be detected by methods known in the art. For example, radioactive labels can be detected using photographic film or scintillation counter, and fluorescent labels can be detected using photodetector to detect emitted light. Enzyme labels are generally detected by providing a substrate and detecting a product produced by the action of the enzyme on the substrate, and thermometric labels are detected by simple visualization of a colored label. In certain embodiments, such labels can be adapted for use in immunological detection (e.g., enzyme-linked immunoassay, radioimmunoassay, fluorescent immunoassay, chemiluminescence immunoassay, etc.). In certain embodiments, the detectable label as described above can be attached to the antibody or antigen-binding fragment thereof of the present invention via a linker of various lengths to reduce potential steric hindrance.

Bispecific or Multispecific Molecules

The antibody or antigen-binding fragment thereof of the present invention can be used to form a bispecific or multispecific molecule. The antibody or antigen-binding fragment thereof of the present invention may be part of a bispecific or multispecific molecule, and the bispecific or multispecific molecule comprises a second functional module (e.g., a second antibody) that is different from the antibody or antigen-binding fragment thereof of the present invention in binding specificity, thereby being able to bind to at least two different binding sites and/or target molecules. For example, the antibody or antigen-binding fragment thereof of the present invention may be linked to a second antibody or antigen-binding fragment thereof that is capable of specifically binding to any protein that may be used as a potential target for combination therapy. To generate the bispecific or multispecific molecule, the antibody or antigen-binding fragment thereof of the present invention may be linked (e.g., by chemical conjugation, gene fusion, non-covalent association, or otherwise) to one or more other binding molecules (e.g., additional antibody, antibody fragment, peptide or binding mimetic).

Thus, in another aspect, the present invention provides a bispecific or multispecific molecule comprising the antibody or antigen-binding fragment thereof of the present invention.

In certain preferred embodiments, the bispecific or multispecific molecule specifically binds to CLDN6 and additionally specifically binds to one or more other targets.

In certain preferred embodiments, the bispecific or multispecific molecule further comprises at least one molecule (e.g., a second antibody) having a second binding specificity for a second target.

Immunoconjugate

The antibody or antigen-binding fragment thereof of the present invention can be linked to a therapeutic agent to form an immunoconjugate. Due to the ability of an immunoconjugate to selectively deliver one or more therapeutic agents to target tissues (e.g., tumor-associated antigens, such as tumors expressing CLDN6 and/or CLDN9), immunoconjugate can enhance the therapeutic efficacy of the antibody or antigen-binding fragment thereof of the present invention in the treatment of a disease (e.g., a cancer).

Accordingly, in another aspect, the present invention provides an immunoconjugate comprising the antibody or antigen-binding fragment thereof of the present invention and a therapeutic agent linked to the antibody or antigen-binding fragment thereof.

In certain preferred embodiments, the immunoconjugate is an antibody-drug conjugate (ADC).

In certain preferred embodiments, the therapeutic agent is a cytotoxic agent. In the present invention, the cytotoxic agent includes any agent that is harmful to a cell (e.g., kills a cell).

In certain preferred embodiments, the therapeutic agent is selected from the group consisting of alkylating agent, mitotic inhibitor, antitumor antibiotic, antimetabolite, topoisomerase inhibitor, tyrosine kinase inhibitor, radionuclide agent, and any combination thereof.

Examples of alkylating agent useful in the immunoconjugate of the present invention include, but are not limited to, nitrogen mustard (e.g., mechlorethamine, chlorambucil, melphalan, cyclophosphamide, etc.), ethyleneimine (e.g., thiotepa, etc.), sulfate ester and polyol (e.g., busulfan, dibromomannitol), nitrosourea (e.g., carmustine, lomustine, etc.), platinum-based antitumor agent (e.g., cisplatin, oxaliplatin, carboplatin, etc.), etc.

Examples of mitotic inhibitor useful in the immunoconjugate of the present invention include, but are not limited to, maytansinoids (e.g., maytansine, maytansinol, C-3 ester of maytansinol, etc.), taxane (e.g., docetaxel, paclitaxel or nanoparticle paclitaxel, etc.), vinca alkaloid (e.g., vindesine sulfate, vincristine, vinblastine or vinorelbine, etc.).

Examples of antitumor antibiotic useful in the immunoconjugate of the present invention include, but are not limited to, actinomycin, anthracycline (e.g., daunorubicin, doxorubicin, epirubicin, idarubicin, etc.), calicheamicin, duocarmycin, etc.

Examples of antimetabolite useful in the immunoconjugate of the present invention include, but are not limited to, folic acid antagonist (e.g., methotrexate, etc.), pyrimidine antagonist (e.g., 5-fluorouracil, floxuridine, cytarabine, capecitabine, gemcitabine, etc.), purine antagonist (e.g., 6-mercaptopurine, 6-thioguanine, etc.), adenosine deaminase inhibitor (e.g., cladribine, fludarabine, nelarabine, pentostatin, etc.).

Examples of topoisomerase inhibitor useful in the immunoconjugate of the present invention include, but are not limited to camptothecin and derivative thereof (e.g., irinotecan, topotecan, etc.), amsacrine, daunomycin, adriamycin, epipodophyllotoxin, ellipticines, epirubicin, etoposide, razoxane, teniposide, etc.

Examples of tyrosine kinase inhibitor useful in the immunoconjugate of the present invention include, but are not limited to, axitinib, bosutinib, cediranib, dasatinib, erlotinib, gefitinib, imatinib, lapatinib, lytotinib, nilotinib, semaxanib, sunitinib, vandetanib, etc.

Examples of radionuclide agent useful in the immunoconjugate of the present invention include, but are not limited to, $^{131}I$, $^{111}In$, $^{90}Y$, $^{177}Lu$, and the like.

In certain exemplary embodiments, the therapeutic agent is selected from the group consisting of platinum-based antineoplastic agents, anthracycline antibiotics, taxane compounds, nucleoside analogs, camptothecin compounds, and analogs or homologues thereof, and any combination thereof.

In certain preferred embodiments, the antibody or antigen-binding fragment thereof of the present invention is conjugated to the therapeutic agent, optionally via a linker.

In the present invention, the cytotoxic agent can be conjugated to the antibody or antigen-binding fragment thereof of the present invention using linker techniques existing in the art. Examples of linker types that have been used to conjugate cytotoxic agents to antibodies include, but are not limited to, hydrazone, thioether, ester, disulfide, and peptide-containing linkers. The selected linker may be, for example, prone to cleavage by low pH within lysosomal compartment or by proteases (e.g., proteases expressed preferentially in tumor tissue, such as cathepsins, such as cathepsins B, C, D).

Further discussion of types of cytotoxic agents, linkers, and methods of conjugating therapeutic agents to antibodies can also be found in Saito, G. et al. (2003) Adv. Drug Deliv. Rev. 55: 199-215; Trail, P. A. et al. (2003) Cancer Immunol. Immunother. 52: 328-337; Payne, G. (2003) Cancer Cell 3: 207-212; Allen, T. M. (2002) Nat. Rev. Cancer 2: 750-763; Pastan, I. and Kreitman, R. J. (2002) Curr. Opin. Investig. Drugs 3: 1089-1091; Senter, P. D. and Springer, C. J. (2001) Adv. Drug Deliv. Rev. 53: 247-264.

Chimeric Antigen Receptor

The antibody or antigen-binding fragment thereof of the present invention can be used to construct a chimeric antigen receptor (CAR), which comprises an extracellular antigen-binding domain (e.g., scFv) that is capable of specific binding to CLDN6 and/or CLDN9, linking to transmembrane domain, and linking to one or more intracellular T cell signaling domain. The intracellular T cell signaling domain can comprise, for example, a T cell receptor signaling domain, a T cell co-stimulatory signaling domain, or a combination thereof. The T cell receptor signaling domain refers to a portion of CAR that comprises the intracellular domain (e.g., the intracellular portion of CD3ζ protein) of T cell receptor. The co-stimulatory signaling domain refers to a portion of CAR that comprises the intracellular domain of co-stimulatory molecule, and the co-stimulatory molecule is a cell surface molecule other than antigen receptors or ligands thereof required for efficient lymphocyte response to antigens.

Features of the CAR of the present invention comprises an ability to direct T-cell specificity and reactivity toward a cell expressing CLDN6 and/or CLDN9 (e.g., a tumor cell) in a non-MHC-restricted manner. The non-MHC-restricted CLDN6 and/or CLDN9 recognition ability endows a T cell expressing the CAR of the present invention with the ability to recognize antigens that is independent to antigen processing.

Accordingly, in another aspect, the present invention provides a chimeric antigen receptor (CAR) comprising an antigen-binding domain of the antibody or antigen-binding fragment thereof of the present invention.

In certain preferred embodiments, the antigen-binding domain comprises a heavy chain variable region and a light chain variable region of the antibody or antigen-binding fragment thereof of the present invention.

In certain preferred embodiments, the antigen-binding domain is a scFv.

In certain preferred embodiments, the chimeric antigen receptor comprises the antigen-binding fragment (e.g., scFv) of the antibody of the present invention.

In certain preferred embodiments, the chimeric antigen receptor is expressed by an immune effector cell (e.g., a T cell).

In certain preferred embodiments, a spacer domain comprising a polypeptide sequence may exist between the antigen-binding domain and the transmembrane domain of the CAR. The spacer domain may comprise up to 300 amino acids, preferably 10 to 100 amino acids, and most preferably 25 to 50 amino acids. In some embodiments, the spacer domain may comprise an immunoglobulin domain, for example, a human immunoglobulin sequence. In certain exemplary embodiments, the immunoglobulin domain comprises immunoglobulin CH2 and CH3 domain sequences. In such embodiments, without being bound by a particular theory, it is believed that the CH2 and CH3 domains extend the antigen-binding domain of the CAR from the membrane of the CAR-expressing cell and more accurately mimic the size and domain structure of a native TCR.

In certain preferred embodiments, the transmembrane domain may be derived from a natural or synthetic source. In such embodiments, the domain may be derived from any membrane-bound or transmembrane protein. Exemplary transmembrane domains useful in the CAR of the present invention may comprise at least transmembrane regions of α, β or ζ chain of a T cell receptor, and the T cell receptor may be selected from the group consisting of CD28, CD3c, CD45, CD4, CD5, CDS, CD9, CD16, CD22, CD33, CD37, CD64, CD80, CD86, CD134, CD137, CD154. Alternatively, the transmembrane domain may be synthetic, in which case it will primarily comprise hydrophobic residues such as leucine and valine.

In certain exemplary embodiments, the transmembrane domain comprises a transmembrane domain of a T cell receptor, for example, a CD8 transmembrane domain.

In certain exemplary embodiments, the transmembrane domain comprises a transmembrane domain of a T cell co-stimulatory molecule (e.g., CD137 or CD28).

In certain preferred embodiments, examples of intracellular T cell domains useful in the CAR include cytoplasmic sequences and co-stimulatory molecules of a T cell receptor (TCR), wherein the T cell receptor (TCR) cytoplasmic sequences and co-stimulatory molecules cooperate to initiate signal transduction following antigen receptor engagement, and any derivatives or variants of these sequences and any synthetic sequences having the same functional capabilities.

In certain preferred embodiments, the intracellular region of the CAR may comprise a primary cytoplasmic signal sequence acting in a stimulatory manner, which may comprise what is known as an immunoreceptor tyrosine-based activation motif or ITAM signal motif. Examples of ITAM comprising a primary cytoplasmic signal sequence that can be included in the CAR include those from CD3ζ, FcRγ, FcRβ, CD3γ, CD3δ, CD3ε, CDS, CD22, CD79a, CD79b, and CD66d proteins.

In certain preferred embodiments, the intracellular region of the CAR may comprise an ITAM comprising a primary cytoplasmic signaling domain (e.g., CD3ζ) itself or in combination with any other desired cytoplasmic domain that can be used in the context of the CAR. For example, the cytoplasmic domain of the CAR comprises a CD3ζ chain portion and an intracellular co-stimulatory signaling domain. The co-stimulatory signaling domain refers to a portion of the CAR comprising the intracellular domain of the co-stimulatory molecule. The co-stimulatory molecule is a cell surface molecule other than antigen receptors or ligands thereof that are required for efficient lymphocyte responses to antigens. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C and B7-H3.

In certain preferred embodiments, the CAR may comprise a CD3 signaling domain, a CD8 signaling domain, a CD28 signaling domain, a CD137 signaling domain, or any combination thereof. The order of the one or more T cell signaling domains on the CAR can be changed by those skilled in the art as needed.

Methods of generating chimeric antigen receptors, T cells comprising such receptors, and their uses (e.g., uses for the treatment of cancers) are known in the art, and described in detail, for example, in Brentjens et al., 2010, Molecular Therapy, 18: 4,666-668; Morgan et al., 2010, Molecular Therapy, published online Feb. 23, 2010, pp. 1-9; Till et al., 2008, Blood, 112: 2261-2271; Park et al., Trends Biotechnol., 29: 550-557,2011; Grupp et al., NEnglJMed., 368: 1509-1518, 2013; Han et al., J. Hematol Oncol., 6: 47, 2013; PCT Patent Publication WO2012/079000, WO2013/126726; and U.S. Patent Publication 2012/0213783, all of which are incorporated herein by reference in their entirety. For example, a nucleic acid molecule encoding the chimeric antigen-binding receptor of the present invention can be included in an expression vector (e.g., a lentiviral vector) for expression in a host cell such as a T cell to produce the CAR. In certain exemplary embodiments, the method of using the chimeric antigen receptor comprises isolating a T cell from a subject, transforming the T cell with an expression vector (e.g., a lentiviral vector) encoding the chimeric antigen receptor, and administering the engineered T cell expressing the chimeric antigen receptor to a subject for therapy, for example, for treating a tumor in the subject.

Accordingly, in another aspect, the present invention provides an isolated nucleic acid molecule comprising a nucleotide sequence encoding the chimeric antigen receptor of the present invention. In certain preferred embodiments, the isolated nucleic acid molecule encodes the chimeric antigen receptor of the present invention.

In another aspect, the present invention provides a vector (e.g., a cloning vector or an expression vector) comprising the isolated nucleic acid molecule as described above. In certain preferred embodiments, the vector of the present invention is, for example, a plasmid.

In another aspect, the present invention provides a host cell comprising the isolated nucleic acid molecule or the vector as described above. In certain preferred embodiments, the host cell is a T cell. In certain preferred embodiments, the host cell is a chimeric antigen receptor T cell (CAR-T).

Therapeutic Method and Pharmaceutical Composition

The antibody or antigen-binding fragment thereof of the present invention can induce ADCC and/or CDC by binding to CLDN6 and/or CLDN9 to kill a cell, and thus can be used to prevent and/or treat a tumor.

Therefore, in another aspect, the present invention provides a pharmaceutical composition comprising the antibody or antigen-binding fragment thereof, the bispecific or multispecific molecule, or the immunoconjugate of the present invention, and a pharmaceutically acceptable carrier and/or excipient.

In certain preferred embodiments, the pharmaceutical composition may further comprise an additional pharmaceutically active agent.

In certain preferred embodiments, the additional pharmaceutically active agent is a drug having antineoplastic activity, such as alkylating agent, mitotic inhibitor, antineoplastic antibiotic, antimetabolite, topoisomerase inhibitor, tyrosine kinase inhibitor, radionuclide agent, radiosensitizer (e.g., gemcitabine, 5-fluorouracil, taxane, cisplatin, etc.), anti-angiogenic agent, cytokine (e.g., GM-CSF, IL-7, IL-12. IL-15, IL-18, IL-21, etc.), molecular targeted drug (e.g., CD20 antibody such as rituximab, Her2 antibody such as trastuzumab, VEGF antibody such as bevacizumab, EGFR antibody such as cetuximab, etc.), immune checkpoint inhibitor (e.g., PD-1 antibody, PD-L1 antibody, CTLA-4 antibody, LAG-3 antibody, etc.), oncolytic virus, etc.

In certain preferred embodiments, in the pharmaceutical composition, the antibody or antigen-binding fragment thereof, bispecific or multispecific molecule, or immunoconjugate of the present invention and the additional pharmaceutically active agent are provided as separate components or provided as components of the same composition. Accordingly, the antibody or antigen-binding fragment thereof, bispecific or multispecific molecule, or immunoconjugate of the present invention and the additional pharmaceutically active agent may be administered simultaneously, separately or sequentially.

In certain exemplary embodiments, the pharmaceutical composition comprises a sterile injectable liquid (e.g., aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v) NaCl), dextrose solution (e.g., 5% dextrose), surfactant-containing solution (e.g., 0.01% polysorbate 20), pH buffered solution (e.g., phosphate buffered saline), Ringer's solution, and any combination thereof.

In another aspect, the present invention provides a method for reducing expression of CLDN6 and/or CLDN9 on the surface of a cell, which comprises contacting the cell with the antibody or antigen-binding fragment thereof, bispecific or multispecific molecule, immunoconjugate, or pharmaceutical composition of the present invention such that the expression of CLDN6 and/or CLDN9 on the surface of the cell is reduced; wherein, the cell expresses CLDN6 and/or CLDN9 on the surface of the cell.

In certain preferred embodiments, the cell is a tumor cell expressing CLDN6 and/or CLDN9.

In certain preferred embodiments, the method is used to reduce the expression of CLDN6 and/or CLDN9 on the cell surface in vitro for non-diagnostic purposes.

In another aspect, there is provided a use of the antibody or antigen-binding fragment thereof, bispecific or multispecific molecule, immunoconjugate, or pharmaceutical composition of the present invention in the manufacture of a medicament for reducing the expression of CLDN6 and/or CLDN9 on a cell surface.

In another aspect, the antibody or antigen-binding fragment thereof, bispecific or multispecific molecule, immunoconjugate, or pharmaceutical composition of the present invention is provided for reducing the expression of CLDN6 and/or CLDN9 on a cell surface.

In another aspect, the present invention provides a method for inhibiting growth of a tumor cell expressing CLDN6 and/or CLDN9 and/or killing the tumor cell, which comprises contacting the tumor cell with an effective amount of the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cell (CAR-T)) of the present invention.

The method can be used for a therapeutic purpose, or for a non-therapeutic purpose. In some preferred embodiments, the method can be used for a non-therapeutic purpose, the method is used to inhibit growth of a tumor cell expressing CLDN6 and/or CLDN9 and/or kill the tumor cell in vitro.

In another aspect, the present invention provides a use of the antibody or antigen-binding fragment thereof, bispecific or multispecific molecule, immunoconjugate, pharmaceutical composition, chimeric antigen receptor or protein expressing the chimeric antigen receptor, host cell (e.g., chimeric antigen receptor T cell (CAR-T)) of the present invention in the manufacture of a medicament for inhibiting growth of a tumor cell expressing CLDN6 and/or CLDN9 and/or killing the tumor cell.

In another aspect, the antibody or antigen-binding fragment thereof, bispecific or multispecific molecule, immunoconjugate, pharmaceutical composition, chimeric antigen receptor or protein expressing the chimeric antigen receptor, host cell (e.g., chimeric antigen receptor T cell (CAR-T)) of the present invention is provided for inhibiting growth of a tumor cell expressing CLDN6 and/or CLDN9 and/or killing the tumor cell.

In another aspect, the present invention provides a method for preventing and/or treating a tumor in a subject (e.g., a human), the method comprising administering to the subject in need thereof an effective amount of the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cells (CAR-T)) of the present invention.

In certain preferred embodiments, the tumor refers to a tumor cell expressing CLDN6 and/or CLDN9. In certain preferred embodiments, the CLDN6 and/or CLDN9 is expressed on the surface of the tumor cell.

In certain preferred embodiments, the tumor expresses CLDN6 and/or CLDN9.

In certain preferred embodiments, the tumor is selected from the group consisting of ovarian cancer, testicular cancer, gastric cancer, endometrial cancer, lung cancer, esophageal cancer, pancreatic cancer, bronchial cancer, breast cancer, ear nose throat (ENT) cancer, colon cancer, liver cancer, head and neck cancer, gallbladder cancer and metastasis thereof (e.g., gastric cancer metastasis, Krukenberg tumor, peritoneal metastasis, or lymph node metastasis).

In certain preferred embodiments, the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cell (CAR-T)) of the present invention is used in combination with an additional drug with an anti-tumor activity. The additional drug with an anti-tumor activity may be administered before, at the same time or after the administration of the antibody or antigen-binding fragment thereof, bispecific or multispecific molecule, immunoconjugate, pharmaceutical composition, chimeric antigen receptor, or host cell expressing the chimeric antigen receptor (e.g., CAR-T).

In certain preferred embodiments, the antibody or antigen-binding fragment thereof, bispecific or multispecific molecule, immunoconjugate, pharmaceutical composition, chimeric antigen receptor, or host cell expressing the chimeric antigen receptor (e.g., CAR-T) is administered in combination with an additional therapy. The additional therapy can be any therapy known to be used on tumors, such as surgery, chemotherapy, radiation therapy, targeted therapy, immunotherapy, hormone therapy, gene therapy or palliative care. The additional therapy may be administered before, at the same time or after the administration of the antibody or antigen-binding fragment thereof, bispecific or multispecific molecule, immunoconjugate, pharmaceutical composition, chimeric antigen receptor, or host cell expressing the chimeric antigen receptor (e.g., CAR-T).

The antibody or antigen-binding fragment thereof, bispecific or multispecific molecule, immunoconjugate, pharmaceutical composition, chimeric antigen receptor, or host cell (e.g., T cell) expressing the chimeric antigen receptor of the present invention can be formulated into any dosage form known in the medical field, for example, tablet, pill, suspension, emulsion, solution, gel, capsule, powder, granule, elixir, lozenge, suppository, injection (including liquid, sterile powder for injection and concentrated solution for injection), inhalation, spray, etc. The preferred dosage form depends on the intended mode of administration and therapeutic use. The pharmaceutical composition of the present invention should be sterile and stable under the conditions of manufacture and storage. A preferred dosage form is injection. Such injection can be a sterile injectable solution. For example, sterile injectable solution can be prepared by incorporating the necessary dose of the antibody of the present invention into an appropriate solvent, and optionally, simultaneously incorporating other desired ingredients (including, but not limited to, pH adjusting agent, surfactant, adjuvant, ionic strength enhancer, isotonic agent, preservative, diluent, or any combination thereof), followed by filter sterilization. In addition, the sterile injectable solution can be prepared as a sterile lyophilized powder (e.g., by vacuum drying or freeze-drying) for ease of storage and use. Such sterile lyophilized powder can be dispersed in a suitable vehicle before use, such as water for injection (WFI), bacteriostatic water for injection (BWFI), sodium chloride solution (e.g. 0.9% (w/v) NaCl), dextrose solution (e.g., 5% dextrose), surfactant-containing solution (e.g., 0.01% polysorbate 20), pH buffer solution (e.g., phosphate buffered saline), Ringer's solution and any combination thereof.

In addition, the antibody or antigen-binding fragment thereof, bispecific or multispecific molecule, immunoconjugate, pharmaceutical composition, chimeric antigen receptor or host cell (e.g., T cell) expressing the chimeric antigen receptor may be presented in the pharmaceutical composition in unit dosage form for ease of administration.

The antibody or antigen-binding fragment thereof, bispecific or multispecific molecule, immunoconjugate, pharmaceutical composition, chimeric antigen receptor, or host cell (e.g., T cell) expressing the chimeric antigen receptor of the present invention can be administrated by any suitable method known in the art, including, but not limited to, oral, buccal, sublingual, ocular, topical, parenteral, rectal, intrathecal, intracytoplasmic reticulum, inguinal, intravesical, topical (e.g., for powder, ointment, or drops), or nasal route. However, for many therapeutic uses, the preferred route/mode of administration is parenteral (e.g., intravenous or bolus injection, subcutaneous injection, intraperitoneal injection, intramuscular injection). The skilled artisan will understand that the route and/or mode of administration will vary depending on the intended purpose. In a preferred embodiment, the antibody or antigen-binding fragment thereof, bispecific or multispecific molecule, immunoconjugate, pharmaceutical composition, chimeric antigen receptor or host cell (e.g., T cell) expressing the chimeric antigen receptor of the present invention is administrated by intravenous injection or bolus injection.

The pharmaceutical composition of the present invention may comprise a "therapeutically effective amount" or "prophylactically effective amount" of the antibody or antigen-binding fragment thereof, bispecific or multispecific molecule, immunoconjugate, pharmaceutical composition, chimeric antigen receptor or host cell (e.g., T cell) expressing the chimeric antigen receptor. "Prophylactically effective amount" refers to an amount sufficient to prevent, arrest, or delay the onset of a disease. "Therapeutically effective amount" refers to an amount sufficient to cure or at least partially prevent the disease and its complications in a patient already suffering from the disease. The therapeutically effective amount of the antibody or antigen-binding fragment thereof of the present invention may vary depending on the severity of the disease to be treated, the general state of the patient's own immune system, the general conditions of the patient such as age, weight and sex, the administration mode, and other therapies administered at the same time, etc.

In the present invention, the dosing regimen can be adjusted to obtain the optimum desired response (e.g., therapeutic or prophylactic response). For example, a single dose can be administered, multiple doses can be administered over time, or the dose can be proportionally reduced or increased as indicated by the exigencies of the therapeutic situation.

In the present invention, the subject may be a mammal, such as a human.

Detection Method and Kit

The antibody or antigen-binding fragment thereof of the present invention can specifically bind to CLDN6 and/or CLDN9, and thus can be used to detect the presence or level of CLDN6 and/or CLDN9 in a sample.

Accordingly, in another aspect, the present invention provides a kit comprising the antibody or antigen-binding fragment thereof of the present invention. In certain preferred embodiments, the antibody or antigen-binding fragment thereof of the present invention comprises a detectable label. In a preferred embodiment, the kit further comprises a second antibody that specifically recognizes the antibody or antigen-binding fragment thereof of the present invention. Preferably, the second antibody further comprises a detectable label.

In the present invention, the detectable label can be any substance detectable by fluorescent, spectroscopic, photochemical, biochemical, immunological, electrical, optical or chemical means. It is especially preferred that such labels are suitable for use in immunological assays (e.g. ELISA, radioimmunoassay, fluorescent immunoassay, chemiluminescent immunoassay, etc.). Such labels are well known in the art and include, but are not limited to, enzymes (e.g., horseradish peroxidase, alkaline phosphatase, β-galactosidase, urease, glucose oxidase, etc.), radionuclides (e.g., $^{3}H$, $^{125}I$, $^{35}S$, $^{14}C$, or $^{32}P$), fluorescent dyes (e.g., fluorescein isothiocyanate (FITC), fluorescein, tetramethylrhodamine isothiocyanate (TRITC), phycoerythrin (PE), Texas Red, rhodamine, quantum dots or cyanine dye derivatives (e.g., Cy7, Alexa 750)), luminescent substances (e.g., chemiluminescent substances, such as acridinium ester compounds), magnetic beads (e.g., Dynabeads®), calorimetric markers such as colloid gold or colored glass or plastic (e.g., polystyrene, polypropylene, latex, etc.) beads, and biotin for binding to the above-mentioned label-modified avidin (e.g., streptavidin). Patents that teach the use of such labels include, but are not limited to, U.S. Pat. Nos. 3,817,837; 3,850,752; 3,939,350; 3,996,345; 4,277,437; 4,275,149; and 4,366,241 (all of which are incorporated herein by reference in their entirety). The detectable labels as described above can be detected by methods known in the art. For example, radioactive labels can be detected using photographic film or scintillation counter, and fluorescent labels can be detected using photodetector to detect emitted light. Enzyme labels are generally detected by providing a substrate and detecting a product produced by the action of the enzyme on the substrate, and thermometric labels are detected by simple visualization of a colored label. In certain embodiments, the detectable label as described above can be attached to the antibody or antigen-binding fragment thereof of the present invention via a linker of various lengths to reduce potential steric hindrance.

In another aspect, the present invention provides a method for detecting the presence or amount of CLDN6 and/or CLDN9 in a sample, comprising the steps of:

(1) contacting the sample with the antibody or antigen-binding fragment thereof of the present invention;

(2) detecting formation of a complex comprising the antibody or antigen-binding fragment thereof and CLDN6 and/or CLDN9 or detecting an amount of the complex.

The formation of the complex indicates the presence of CLDN6 and/or CLDN9 or a cell expressing CLDN6 and/or CLDN9.

In certain preferred embodiments, the sample is a cellular sample, i.e., a sample comprising a cell (e.g., tumor cell). In such embodiments, preferably, the complex is formed between the antibody, antigen-binding fragment or conjugate and CLDN6 and/or CLDN9 expressed by the cell in the sample.

In a preferred embodiment, the antibody or antigen-binding fragment thereof of the present invention further comprises a detectable label. In another preferred embodiment, in step (2), the antibody or antigen-binding fragment thereof of the present invention is detected using an agent comprising a detectable label.

The method can be used for a diagnostic purpose, or a non-diagnostic purpose (e.g., the sample is a sample of cells rather than a sample from a patient). In certain preferred embodiments, the CLDN6 and/or CLDN9 is human CLDN6 and/or CLDN9.

In another aspect, provided is a use of the antibody or antigen-binding fragment thereof of the present invention in the manufacture of a kit for detecting the presence or amount of CLDN6 and/or CLDN9 in a sample. In certain preferred embodiments, the CLDN6 and/or CLDN9 is human CLDN6 and/or CLDN9.

In another aspect, the present invention provides a method for determining whether a tumor can be treated by an anti-tumor therapy targeting CLDN6 and/or CLDN9, which comprises the following steps:

(1) contacting a sample containing a cell of the tumor with the antibody or antigen-binding fragment thereof of the present invention;

(2) detecting formation of a complex comprising the antibody or antigen-binding fragment thereof and CLDN6 and/or CLDN9.

In certain preferred embodiments, the complex is formed between the antibody or antigen-binding fragment thereof and CLDN6 and/or CLDN9 expressed by the tumor cell in the sample.

In certain preferred embodiments, the sample is from a subject who has, is suspected of having, or is at risk of having a tumor. In certain preferred embodiments, the sample is from a tissue or organ in which cells do not substantially express CLDN6 and/or CLDN9 when the tissue or organ is not cancerous. In certain preferred embodiments, the tissue is selected from the group consisting of gastric tissue, lung tissue, esophageal tissue, pancreatic tissue or breast tissue, and the tissue has optionally been diagnosed as being affected by cancer, for example, which is diagnosed by visual inspection or culture testing of the tissue or organ cells. In certain preferred embodiments, the tissue is a tissue other than gastric tissue. In certain preferred embodiments, the tissue is lung tissue, esophageal tissue, pancreatic tissue or breast tissue. In such embodiments, when there are CLDN6 and/or CLDN9 or cells expressing CLDN6 and/or CLDN9, and/or when the amount of CLDN6 and/or CLDN9 or cells expressing CLDN6 and/or CLDN9 increases as compared to a reference level (e.g., compared to a patient without a neoplastic disease), it is indicated that the subject is suitable for the anti-tumor therapy targeting CLDN6 and/or CLDN9.

In a preferred embodiment, the antibody or antigen-binding fragment thereof of the present invention further comprises a detectable label. In another preferred embodiment, in step (2), the antibody or antigen-binding fragment thereof of the present invention is detected using an agent comprising a detectable label.

In certain preferred embodiments, the CLDN6 and/or CLDN9 is human CLDN6 and/or CLDN9.

In certain preferred embodiments, the tumor is selected from the group consisting of ovarian cancer, testicular cancer, gastric cancer, endometrial cancer, lung cancer, esophageal cancer, pancreatic cancer, bronchial cancer, breast cancer, ear nose throat (ENT) cancer, colon cancer, liver cancer, head and neck cancer, gallbladder cancer and metastases thereof (e.g., gastric cancer metastases such as Krukenberg tumor, peritoneal metastases, or lymph node metastases).

In another aspect, provided is a use of the antibody or antigen-binding fragment thereof of the present invention in the manufacture of a kit for determining whether a tumor can be treated by an anti-tumor therapy targeting CLDN6 and/or CLDN9.

In certain preferred embodiments, the antibody or antigen-binding fragment thereof comprises a detectable label.

In certain preferred embodiments, the CLDN6 and/or CLDN9 is human CLDN6 and/or CLDN9.

In certain preferred embodiments, the tumor is selected from the group consisting of ovarian cancer, testicular cancer, gastric cancer, endometrial cancer, lung cancer, esophageal cancer, pancreatic cancer, bronchial cancer, breast cancer, ear nose throat (ENT) cancer, colon cancer, liver cancer, head and neck cancer, gallbladder cancer and metastases thereof (e.g., gastric cancer metastases such as Krukenberg tumor, peritoneal metastases, or lymph node metastases).

Definition of Terms

In the present invention, unless otherwise specified, the scientific and technical terms used herein have the meanings commonly understood by those skilled in the art. In addition, the operation steps in cell culture, biochemistry, nucleic acid chemistry, and immunology laboratories used here are all routine steps widely used in the corresponding fields. Meanwhile, in order to better understand the present invention, definitions and explanations of relevant terms are provided below.

As used herein, the term "CLDN6 (Claudin 6)" has the meaning generally understood by those skilled in the art, which belongs to the claudin family, is a transmembrane protein in the tight junction of epithelium and endothelium, and may be involved in autophagy. The sequence of CLDN6 is well known in the art, and can be referred to NCBI database accession number P56747. As used herein, the term "CLDN9 (Claudin 9)" has the meaning generally understood by those skilled in the art, which belongs to the claudin family and is a transmembrane protein in the tight junction between epithelium and endothelium. The sequence of CLDN9 is well known in the art, and can be referred to NCBI database accession number 095484.

As used herein, the term "antibody" refers to an immunoglobulin molecule generally composed of two pairs of polypeptide chains (each pair having one light chain (LC) and one heavy chain (HC)). Antibody light chains can be classified as κ (kappa) and λ (lambda) light chains. Heavy chains can be classified as μ, δ, γ, α, or ε, and the isotypes of antibody can be defined as IgM, IgD, IgG, IgA, and IgE, respectively. In the light and heavy chains, the variable and constant regions are linked by a "J" region of about 12 or more amino acids, and the heavy chain also contains a "D" region of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain, CL. Constant domain is not directly involved in the binding of antibody to antigen, but exhibits a variety of effector functions, such as mediating immunoglobulin with host tissue or factor, including the binding of various cells (e.g., effector cells) of immune system to the first component (C1q) of classical complement system. The VH and VL regions can also be subdivided into regions of high variability (also called as complementarity determining regions (CDRs)), which are interspersed with more conserved regions called framework regions (FRs). Each of VH and VL consists of 3 CDRs and 4 FRs arranged in the following order: FR1, CDR1, FR2, CDR2, FR3, CDR3, FR4 from amino terminus to carboxy terminus. The variable regions (VH and VL) of each heavy chain/light chain pair respectively form the antigen binding site. The assignment of amino acids to regions or domains can follow Kabat, Sequences of Proteins of Immunological Interest (National Institutes of Health, Bethesda, Md. (1987 and 1991)), or Chothia & Lesk (1987) J. Mol. Biol. 196: 901-917; definition by Chothia et al. (1989) Nature 342:878-883.

As used herein, the term "complementarity determining region" or "CDR" refers to the amino acid residues in the variable region of antibody that are responsible for antigen binding. The variable regions of the heavy and light chains each contain 3 CDRs, designated CDR1, CDR2 and CDR3. The precise boundaries of these CDRs can be defined according to various numbering systems known in the art, such as the Kabat numbering system (Kabat et al., Sequences of Proteins of Immunological Interest, 5th Ed. Public Health Service, National Institutes of Health, Bethesda, Md., 1991), the Chothia numbering system (Chothia & Lesk (1987) J. Mol. Biol. 196: 901-917; Chothia et al. (1989) Nature 342: 878-883) or the IMGT numbering system (Lefranc et al. al., Dev. Comparat. Immunol. 27: 55-77, 2003). For a given antibody, those skilled in the art will readily identify the CDRs defined by each numbering system. Also, the correspondence between different numbering systems is well known to those skilled in the art (e.g., see Lefranc et al., Dev. Comparat. Immunol. 27: 55-77, 2003).

In the present invention, the CDRs contained in the antibody or antigen-binding fragment thereof of the present invention can be determined according to various numbering systems known in the art. In certain embodiments, the antibody or antigen-binding fragment thereof of the present invention contain CDRs preferably identified by the Kabat, Chothia or IMGT numbering system. In certain embodiments, the antibody or antigen-binding fragment thereof of the present invention contains CDRs preferably identified by the IMGT numbering system.

As used herein, the term "framework region" or "FR" residues refers to those amino acid residues in an antibody variable region other than the CDR residues as defined above.

The term "antibody" is not limited to any particular method of producing antibodies. For example, it includes recombinant antibody, monoclonal antibody and polyclonal antibody. The antibody can be of a different isotype, for example, can be an IgG (e.g., IgG1, IgG2, IgG3 or IgG4 subtype), IgA1, IgA2, IgD, IgE or IgM antibody.

As used herein, the term "antigen-binding fragment" of antibody refers to a polypeptide of a fragment of an antibody, such as a polypeptide of a fragment of a full-length antibody, which retains the ability to specifically bind the same antigen to which the full-length antibody binds, and/or competes with the full-length antibody for specific binding to the antigen, which is also referred to as an "antigen-binding moiety". See generally, Fundamental Immunology, Ch. 7 (Paul, W., ed., 2nd ed., Raven Press, N.Y. (1989), which is incorporated herein by reference in its entirety for all purposes. The antigen-binding fragment of antibody can generate by recombinant DNA techniques or by enzymatic or chemical cleavage of intact antibody. Non-limiting examples of antigen-binding fragment include Fab, Fab', $F(ab')_2$, Fd, Fv, complementarity determining region (CDR) fragment, single chain antibody (e.g., scFv), chimeric antibody, diabody, linear antibody, nanobody (technology from Domantis), domain antibody (technology from Ablynx), and such polypeptides, which comprises at least a portion of an antibody sufficient to confer specific antigen binding ability on the polypeptide. Engineered antibody variants are reviewed in Holliger et al., 2005; Nat Biotechnol, 23: 1126-1136.

As used herein, the term "full-length antibody" refers to an antibody consisting of two "full-length heavy chains" and two "full-length light chains". Wherein, "full-length heavy chain" refers to a polypeptide chain consisting of a heavy chain variable region (VH), a heavy chain constant region CH1 domain, a hinge region (HR), a heavy chain constant region CH2 domain, a heavy chain constant region CH3 domain in the direction from N-terminal to C-terminal; and, when the full-length antibody is of IgE isotype, which optionally comprises a heavy chain constant region CH4 domain. Preferably, the "full-length heavy chain" is a polypeptide chain consisting of VH, CH1, HR, CH2 and CH3 in the direction from N-terminal to C-terminal. The "full-length light chain" is a polypeptide chain consisting of a light chain variable region (VL) and a light chain constant region (CL) in the N-terminal to C-terminal direction. The two pairs of full-length antibody chains are linked together by a disulfide bond between CL and CH1 and a disulfide bond between the HRs of the two full-length heavy chains. The full-length antibody of the present invention can be from a single species, such as a human; it can also be a chimeric antibody or a humanized antibody. The full-length antibody of the present invention comprises two antigen-binding sites formed by VH and VL pairs, respectively, which specifically recognizes/binds to the same antigen.

As used herein, the term "Fd" refers to an antibody fragment consisting of VH and CH1 domains; the term "dAb fragment" refers to an antibody fragment consisting of VH domains (Ward et al., Nature 341:544 546 (1989)); the term "Fab fragment" refers to an antibody fragment consisting of VL, VH, CL and CH1 domains; the term "$F(ab')_2$ fragment" refers to an antibody fragment comprising two Fab fragments linked by a disulfide bridge on the hinge region; the term "Fab' fragment" refers to a fragment obtained by reducing the disulfide bond that links two heavy chain fragments in $F(ab)_2$ fragment, and consisting of an intact light chain and heavy chain Fd fragment (consisting of VH and CH1 domains).

As used herein, the term "Fv" refers to an antibody fragment consisting of one-armed VL and VH domains of antibody. Fv fragment is generally considered to be the smallest antibody fragment that can form an intact antigen-binding site. It is generally believed that the six CDRs confer antigen-binding specificity to an antibody. However, even a variable region (e.g., an Fd fragment, which contains only 3 antigen-specific CDRs) is able to recognize and bind to an antigen, albeit with possibly lower affinity than the intact binding site.

As used herein, the term "Fc" refers to an antibody fragment formed by binding the second and third constant regions of the first heavy chain to the second and third constant regions of the second heavy chain via a disulfide bond. The Fc fragment of antibody has many different functions, but is not involved in antigen binding.

As used herein, the term "scFv" refers to a single polypeptide chain comprising VL and VH domains, wherein the VL and VH are linked by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Vol. 113, Eds. Roseburg and Moore, Springer-Verlag, New York, pp. 269-315 (1994)). Such scFv molecule can have the general structure: $NH_2$-VL-linker-VH-COOH or $NH_2$-VH-linker-VL-COOH. A suitable linker in the prior art consists of repeated GGGGS amino acid sequences or variants thereof. For example, a linker with the amino acid sequence $(GGGGS)_4$, as well as variant thereof (Holliger et al. (1993) Proc. Natl. Acad. Sci. USA 90: 6444-6448) can be used. Other linkers useful in the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol.

293:41-56 and Roovers et al. (2001), Cancer Immunol. In some cases, a disulfide bond may also exist between the VH and VL of scFv.

As used herein, the term "diabody" refers to that its VH and VL domains are expressed on a single polypeptide chain, but the linker used is too short to allow pairing between the two domains of the same chain, this forces the domains to pair with the complementary domains of the other chain and create two antigen binding sites (see, for example, Holliger P. et al., Proc. Natl. Acad. Sci. USA 90:6444-6448 (1993), and Poljak R. J. et al., Structure 2:1121-1123 (1994)).

As used herein, the term "single-domain antibody (sdAb)" has the meaning commonly understood by those skilled in the art, which refers to an antibody fragment consisting of a single monomer variable antibody domain (e.g., a single heavy chain variable antibody domain) that retains the ability to specifically bind to the same antigen to which the full-length antibody binds. Single-domain antibody is also called nanobody.

As used herein, the term "probody" has the meaning commonly understood by those skilled in the art, which refers to a masked antibody that remains inert in healthy tissue but is specifically activated in a disease environment (e.g., proteolytic cleavage by proteases enriched or unique to the disease environment). Its detailed teaching can be found in, for example, Desnoyers et al., Sci. Transl. Med., 5: 207ra144, 2013. Similar masking techniques can be used with any of the antibodies, or antigen-binding portions thereof, described herein.

Each of the above antibody fragments maintains the ability to specifically bind to the same antigen to which the full-length antibody binds, and/or competes with the full-length antibody for specific binding to the antigen.

Antigen-binding fragments of antibodies (e.g., the antibody fragments described above) can be obtained from a given antibody (e.g., an antibody provided herein) using conventional techniques known to those skilled in the art (e.g., recombinant DNA techniques or enzymatic or chemical cleavage methods), and the antigen-binding fragments of antibodies are screened for specificity in the same manner as for intact antibodies.

Herein, unless the context clearly dictates otherwise, when the term "antibody" is referred to, it includes not only an intact antibody but also an antigen-binding fragment of the antibody.

As used herein, the terms "monoclonal antibody", "McAb", "mAb" have the same meaning and are used interchangeably, and refer to one antibody or one fragment of antibody from a population of highly homologous antibody molecules, that is, a population of identical antibody molecules, except for natural mutations that may occur spontaneously. Monoclonal antibody is are highly specific for a single epitope on an antigen. Polyclonal antibodies are relative to monoclonal antibody, which generally comprise at least two or more different antibodies that generally recognize different epitopes on an antigen. Furthermore, the modifier "monoclonal" only indicates that the antibody is characterized as being obtained from a population of highly homologous antibodies and should not be construed as requiring any particular method to prepare the antibody.

Monoclonal antibodies of the present invention can be prepared by a variety of techniques, such as hybridoma technology (see, for example, Kohler et al. Nature, 256:495, 1975), recombinant DNA technology (see, for example, U.S. Pat. No. 4,816,567), or bacteriophage antibody library technology (see, for example, Clackson et al. Nature 352: 624-628, 1991, or Marks et al. J. Mol. Biol. 222: 581-597, 1991).

The antibody can be purified by known techniques such as affinity chromatography using protein A or protein G. Subsequently or alternatively, a specific antigen (a target molecule recognized by the antibody) or its epitope can be immobilized on a column, and the immunospecific antibody can be purified by immunoaffinity chromatography. The purification of immunoglobulin can refer to, for example, D. Wilkinson (The Scientist, published by The Scientist, Inc., Philadelphia Pa., Vol. 14, No. 8 (Apr. 17, 2000), pp. 25-28).

As used herein, the term "chimeric antibody" refers to an antibody whose light chain and/or heavy chain are partly derived from an antibody (which may be derived from a specific species or belong to a certain antibody class or subclass), and the other part of the light chain or/and heavy chain is derived from another antibody (which may be derived from the same or different species or belong to the same or different antibody class or subclass), but in any case, it still retains the binding activity to the target antigen (U.S. Pat. No. 4,816,567 to Cabilly et al.; Morrison et al., Proc. Natl. Acad. Sci. USA, 81: 6851 6855 (1984)). For example, the term "chimeric antibody" may include such an antibody (e.g., a human-mouse chimeric antibody) in which the antibody's heavy and light chain variable regions are derived from a first antibody (e.g., a murine antibody), and the antibody's heavy and light chain constant regions are derived from a second antibody (e.g., a human antibody).

As used herein, the term "humanized antibody" refers to a genetically engineered non-human antibody, which amino acid sequence has been modified to increase homology to the sequence of a human antibody. Typically, all or part of the CDRs of a humanized antibody are derived from a non-human antibody (a donor antibody), and all or part of the non-CDR regions (e.g., variable FR and/or constant regions) are derived from a human immunoglobulin (a receptor antibody). Humanized antibodies generally retain the expected properties of the donor antibody, including, but not limited to, antigen specificity, affinity, reactivity and the like. The donor antibody can be a mouse, rat, rabbit, or non-human primate (e.g., cynomolgus monkey) antibody with the expected properties (e.g., antigen specificity, affinity, reactivity, etc.).

In the present application, the expected properties of the antibody of the present invention include: (1) specific recognition/binding to CLDN6 and/or CLDN9 (especially human CLDN6 and/or human CLDN9); (2) mediating CLDN6 internalization; (3) inducing killing of a cell expressing human CLDN6 through antibody-dependent cell-mediated cytotoxicity (ADCC); (4) inducing killing of a cell expressing human CLDN6 through complement-dependent cytotoxicity (CDC); (5) ability of preventing and/or treating a tumor. The antibody of the present invention has one or more of the desired properties described above.

The chimeric antibody or humanized antibody of the present invention can be prepared according to the sequence of the mouse monoclonal antibody prepared above. The DNA encoding the heavy and light chains can be obtained from the target murine hybridoma and engineered to contain non-murine (e.g., human) immunoglobulin sequences using standard molecular biology techniques.

In order to prepare the chimeric antibody, murine immunoglobulin variable regions can be linked to human immunoglobulin constant regions using methods known in the art (see, for example, U.S. Pat. No. 4,816,567 to Cabilly et al.).

For example, the DNA encoding VH is operably linked to another DNA molecule encoding the heavy chain constant region to obtain a full-length heavy chain gene. The sequences of human heavy chain constant region genes are known in the art (see, for example, Kabat, E. A. et al. (1991), Sequences of Proteins of Immunological Interest, Fifth Edition, U.S. Department of Health and Human Services, NIH Publication No. 91-3242), and the DNA fragments containing these regions can be obtained by standard PCR amplification. The heavy chain constant region may be IgG1, IgG2, IgG3, IgG4, IgA, IgE, IgM or IgD constant region, but is generally preferably IgG1 or IgG4 constant region. For example, the DNA encoding VL is operably linked to another DNA molecule encoding the light chain constant region CL to obtain a full-length light chain gene (as well as a Fab light chain gene). The sequences of human light chain constant region genes are known in the art (see, for example, Kabat, E. A. et al. (1991), Sequences of Proteins of Immunological Interest, Fifth Edition, U.S. Department of Health and Human Services, NIH Publication No. 91-3242), and the DNA fragments containing these regions can be obtained by standard PCR amplification. The light chain constant region may be κ or λ constant region, but generally and preferably κ constant region.

In order to prepare the humanized antibody, murine CDRs can be inserted into human framework sequences using methods known in the art (see U.S. Pat. No. 5,225,539 to Winter; U.S. Pat. No. 5,530,101 to Queen et al; U.S. Pat. Nos. 5,585,089; 5,693,762 and 6,180,370; and Lo, Benny, K. C., editor, in Antibody Engineering: Methods and Protocols, volume 248, Humana Press, New Jersey, 2004). Alternatively, transgenic animals that are capable of producing no endogenous immunoglobulins following immunization and capable of producing complete human antibody repertoire can also be utilized. For example, it has been reported that the homozygous deletion of antibody heavy chain joining region (JH) gene in chimeric and germline mutant mice could completely suppress the production of endogenous antibody, then the human germline immunoglobulin gene arrays were transferred to the germline mutant mice, and the mice would produce human antibodies upon antigenic stimulation (see, for example, Jakobovits et al., 1993, Proc. Natl. Acad. Sci. USA 90:2551; Jakobovits et al., 1993, Nature 362:255-258; Bruggermann et al., 1993, Year in Immunology 7:33; and Duchosal et al., 1992, Nature 355:258). The non-limiting examples of the transgenic animals include, HuMAb mice (Medarex, Inc.) that contain human immunoglobulin gene miniloci encoding unrearranged human heavy (μ and γ) and κ light chain immunoglobulin sequences, and targeted mutations that inactivate endogenous μ and κ chain loci (see, for example, Lonberg et al. (1994), Nature 368(6474):856-859); or "KM mouse TM" that carries a human heavy chain transgene and human light chain transchromosome (see patent application WO02/43478). Other methods for humanizing antibodies include phage display technology (Hoogenboom et al., 1991, J. Mol. Biol. 227:381; Marks et al., J. Mol. Biol. 1991, 222:581-597; Vaughan et al. Man, 1996, Nature Biotech 14:309).

As used herein, the term "germline antibody gene" or "germline antibody gene segment" refers to a sequence encoding an immunoglobulin present in the genome of an organism, which has not undergone the maturation process of genetic rearrangement and mutation leading to the expression of specific immunoglobulin. In the present invention, the expression "heavy chain germline gene" refers to a germline antibody gene or gene fragment encoding an immunoglobulin heavy chain, which comprises V gene (variable), D gene (diversity), J gene (joining) and C gene (constant); similarly, the expression "light chain germline gene" refers to a germline antibody gene or gene fragment encoding an immunoglobulin light chain, which comprises V gene (variable), J gene (joining) and C gene (constant). In the present invention, the amino acid sequence encoded by the germline antibody gene or germline antibody gene fragment is also referred to as "germline sequence". Germline antibody genes or germline antibody gene fragments and their corresponding germline sequences are well known to those skilled in the art, and can be obtained or queried from professional databases (e.g., IMGT, UNSWIg, NCBI or VBASE2).

As used herein, the term "specific binding" refers to a non-random binding reaction between two molecules, such as the reaction between an antibody and an antigen to which it targets. The strength or affinity of a specific binding interaction can be expressed in terms of the equilibrium dissociation constant ($K_D$) for that interaction. In the present invention, the term "$K_D$" refers to the dissociation equilibrium constant of a specific antibody-antigen interaction, which is used to describe the binding affinity between an antibody and an antigen. The smaller the equilibrium dissociation constant, the tighter the antibody-antigen binding, and the higher the affinity between the antibody and the antigen. In certain embodiments, an antibody that specifically binds to an antigen (or an antibody specific to an antigen) refers to that the antibody binds to the antigen with an affinity ($K_D$) of less than about $10^{-9}$ M, such as less than about $10^{-9}$ M, $10^{-10}$ M, $10^{-11}$ M or $10^{-12}$ M or less. The specific binding properties between two molecules can be determined using methods well known in the art, for example using surface plasmon resonance (SPR) in a BIACORE instrument.

As used herein, the term "cytotoxic agent" comprises any agent that is detrimental to (e.g., kills) a cell, such as chemotherapeutic drug, bacterial toxin, plant toxin, or radioisotope, among others.

As used herein, the term "vector" refers to a nucleic acid delivery vehicle into which a polynucleotide can be inserted. When the vector can express the protein encoded by the inserted polynucleotide, the vector is called as an expression vector. The vector can be introduced into a host cell by transformation, transduction or transfection, so that the genetic material element carried thereby can be expressed in the host cell. Vectors are well known to those skilled in the art and include, but are not limited to: plasmids; phagemid; cosmid; artificial chromosome, such as yeast artificial chromosome (YAC), bacterial artificial chromosome (BAC) or P1 derived artificial chromosome (PAC); phage such as λ phage or M13 phage and animal virus. Animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including, but not limited to, promoter sequence, transcription initiation sequence, enhancer sequence, selection element, and reporter gene. Additionally, the vector may also contain an origin of replication site.

As used herein, the term "host cell" refers to a cell into which a vector can be introduced, which includes, but is not limited to, prokaryotic cell such as *Escherichia coli* or *Bacillus subtilis*, fungal cell such as yeast cells or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

As used herein, the term "identity" is used to refer to the sequence matching between two polypeptides or between two nucleic acids. When a position in both sequences being compared is occupied by the same base or amino acid monomer subunit (e.g., a position in each of two DNA molecules is occupied by an adenine, or a position in each of two polypeptides is occupied by a lysine), then the molecules are identical at that position. The "percent identity" between two sequences is a function of the number of matched positions shared by the two sequences divided by the number of positions compared×100. For example, for two sequences, if 6 out of 10 positions match, the two sequences an identity of 60%. For example, DNA sequences CTGACT and CAGGTT have an identity of 50% (3 out of a total of 6 positions match). Typically, comparison is performed when two sequences are aligned for maximum identity. Such alignment can be accomplished using, for example, the method of Needleman et al. (1970) J. Mol. Biol. 48:443-453, which can be conveniently performed by a computer program such as the Align program (DNAstar, Inc.). The algorithm of E. Meyers and W. Miller (Comput. Appl Biosci., 4:11-17 (1988)), which has been integrated into the ALIGN program (version 2.0), can also be used, in which the PAM120 weight residue table with a gap length penalty of 12 and a gap penalty of 4 can be used, to determine the percent identity between two amino acid sequences. In addition, the algorithm of Needleman and Wunsch (J MoI Biol. 48:444-453 (1970)) in the GAP program integrated into the GCG software package (available at www.gcg.com), can be used, in which the Blossum 62 matrix or PAM250 matrix with gap weight of 16, 14, 12, 10, 8, 6, or 4 and length weight of 1, 2, 3, 4, 5, or 6 can be used, to determine percent identity between two amino acid sequences.

As used herein, the term "conservative substitution" refers to an amino acid substitution that does not adversely affect or alter the intended properties of the protein/polypeptide comprising the amino acid sequence. For example, a conservative substitution can be introduced by standard techniques known in the art such as site-directed mutagenesis and PCR-mediated mutagenesis. Conservative amino acid substitutions include substitutions of amino acid residues with amino acid residues that have similar side chains, e.g., substitution with residues that are physically or functionally similar to the corresponding amino acid residues (e.g., having similar size, shape, charge, chemical properties, including the ability to form covalent bonds or hydrogen bonds, etc.). Families of amino acid residues with similar side chains have been defined in the art. These families include those with basic side chain (e.g., lysine, arginine, and histidine), acidic side chain (e.g., aspartic acid, glutamic acid), uncharged polar side chain (e.g., glycine, asparagine, glutamine, serine, threonine, tyrosine, cysteine, tryptophan), non-polar side chain (e.g., alanine, valine, leucine, isoleucine, proline, phenylalanine, methionine), β branched side chain (e.g., threonine, valine, isoleucine), and aromatic side chain (e.g., tyrosine, phenylalanine, tryptophan, histidine). Therefore, it is preferred to replace the corresponding amino acid residue with another amino acid residue from the same side chain family. Methods for identifying conservative substitutions of amino acids are well known in the art (see, for example, Brummell et al., Biochem. 32:1180-1187 (1993); Kobayashi et al. Protein Eng. 12(10):879-884 (1999) and Burks et al. Proc. Natl Acad. Set USA 94:412-417 (1997), which are incorporated herein by reference).

The twenty conventional amino acids referred to herein have been written following conventional usage. See, for example, Immunology-A Synthesis (2nd Edition, E. S. Golub and D. R. Gren, Eds., Sinauer Associates, Sunderland, Mass. (1991)), which are incorporated herein by reference. In the present invention, the terms "polypeptide" and "protein" have the same meaning and are used interchangeably. And in the present invention, amino acids are generally represented by one-letter and three-letter abbreviations well known in the art. For example, alanine can be represented by A or Ala.

As used herein, the term "chimeric antigen receptor (CAR)" refers to an engineered T cell receptor that has an extracellular antibody-derived targeting domain (e.g., scFv) conjugated to one or more intracellular signaling domains of the T cell receptor. In the present invention, the term "chimeric antigen receptor T cell" is a T cell expressing a CAR and having antigen specificity determined by the targeting domain of the CAR. Methods for producing CARs (e.g., for cancer therapy) are known in the art, see, for example, Park et al., Trends Biotechnol., 29: 550-557, 2011; Grupp et al., NEnglJMed., 368: 1509-1518, 2013; Han et al., J. Hematol Oncol., 6: 47, 2013; PCT Patent Publications WO2012/079000, WO2013/059593; and US Patent Publication 2012/0213783, all of which are incorporated herein by reference in their entirety.

As used herein, the term "pharmaceutically acceptable carrier and/or excipient" refers to a carrier and/or excipient that is pharmacologically and/or physiologically compatible with the subject and the active ingredient. It is well known in the art (see, for example, Remington's Pharmaceutical Sciences. Edited by Gennaro A R, 19th ed. Pennsylvania: Mack Publishing Company, 1995) and includes, but is not limited to: pH adjuster, surfactant, adjuvant, ionic strength enhancing agent, diluent, agent for maintaining osmotic pressure, agent for delaying absorption, preservative. For example, the pH adjusting agent includes, but is not limited to, phosphate buffer. The surfactant includes, but is not limited to, cationic, anionic or nonionic surfactant, such as Tween-80. The ionic strength enhancing agent includes, but is not limited to, sodium chloride. The preservative includes, but is not limited to, various antibacterial and antifungal agent, such as p-hydroxy-benzoate ester, chloretone, phenol, sorbic acid, and the like. The agent for maintaining osmotic pressure includes, but is not limited to, sugar, NaCl, and the like. The agent for delaying absorption includes, but is not limited to, monostearate salt and gelatin. The diluent includes, but is not limited to, water, aqueous buffer (e.g., buffered saline), alcohol and polyol (e.g., glycerol), and the like. The preservative includes, but is not limited to, various antibacterial and antifungal agent, such as thimerosal, 2-phenoxyethanol, paraben, chloretone, phenol, sorbic acid, and the like. The stabilizer has the meaning commonly understood by those skilled in the art, which is capable of stabilizing the desired activity of the active ingredient in the drug, including but not limited to sodium glutamate, gelatin, SPGA, saccharide (e.g., sorbitol, mannitol, starch, sucrose, lactose, glucan, or glucose), amino acid (e.g., glutamic acid, glycine), protein (e.g., dry whey, albumin, or casein) or degradation product thereof (e.g., lactalbumin hydrolyzate), etc. In certain exemplary embodiments, the pharmaceutically acceptable carrier or excipient comprises a sterile injectable liquid (e.g., an aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v)

NaCl), dextrose solution (e.g., 5% dextrose), surfactant-containing solution (e.g., 0.01% polysorbate 20), pH buffered solution (e.g., phosphate buffered saline), Ringer's solution, and any combination thereof.

As used herein, the term "prevention" refers to a method performed to prevent or delay the occurrence of a disease or disorder or symptom (e.g., a tumor) in a subject. As used herein, the term "treatment" refers to a method performed to obtain a beneficial or desired clinical outcome. For the purposes of the present invention, a beneficial or desired clinical outcome includes, but is not limited to, alleviation of symptom, reduction in the extent of disease, stabilization (i.e., not worsening) of disease state, delaying or slowing the progression of disease, amelioration or remission of disease state, and relief of symptom (whether in part or in whole), whether detectable or undetectable. In addition, "treatment" can also mean prolonging survival as compared to expected survival if not receiving treatment.

As used herein, the term "subject" refers to a mammal, such as a primate mammal, such as a human. In certain embodiments, the subject (e.g., human) has a tumor (e.g., a tumor expressing CLDN6 and/or CLDN9), or is at risk of suffering from the above diseases.

As used herein, the term "effective amount" refers to an amount sufficient to obtain, or at least partially obtain, the desired effect. For example, an effective amount for preventing a disease (e.g., a tumor) refers to an amount sufficient to prevent, arrest, or delay the onset of the disease (e.g., tumor); an effective amount for treating a disease refers to an amount sufficient to cure or at least partially prevent the disease and complication thereof in a patient with the disease. Determining such effective amounts is well within the ability of those skilled in the art. For example, an effective amount for therapeutic use will depend on the severity of disease to be treated, the general state of patient's own immune system, the patient's general condition such as age, weight and sex, the mode of administration of drug, and other concurrently administered therapies and so on.

As used herein, the term "immune effector cell" includes a cell of hematopoietic origin and functioning in an immune response, for example lymphocyte, such as B cell and T cell; natural killer cell; myeloid cell, such as monocyte, macrophage, eosinophil, mast cell, basophil, and granulocyte. In certain preferred embodiments, the immune effector cell is a T cell.

As used herein, the term "metastasis" refers to the spread of cancer cells from their original site to other parts of the body. The formation of metastases is a very complex process and depends on the detachment of malignant cells from the primary tumor, invasion of the extracellular matrix, penetration of the endothelial basement membrane to enter body cavities and blood vessels, and subsequent infiltration of target organs after transport by the blood. Finally, the growth of new tumors (i.e, secondary tumors or metastatic tumors) at target sites is dependent on angiogenesis. Tumor metastasis often occurs even after resection of the primary tumor, as tumor cells or components may remain and develop metastatic potential. In one embodiment, the term "metastasis" according to the present invention relates to "distant metastasis", which relates to metastasis away from the primary tumor and the local lymph node system. The cells of a secondary or metastatic tumor resemble those in the original tumor. This means that for example if ovarian cancer metastasizes to the liver, the secondary tumor consists of abnormal ovarian cells (rather than abnormal liver cells). A tumor in the liver is then called metastatic ovarian cancer (not liver cancer).

Beneficial Effects of the Present Invention

Compared with the prior art, the technical solution of the present invention has the following beneficial effects:

the antibody of the present invention can specifically recognize/bind to CLDN6 and/or CLDN9, and can induce the killing of cells expressing CLDN6 (e.g., tumor cells) through ADCC and/or CDC. Therefore, the antibody of the present invention has the potential to be used for the prevention and/or treatment of tumors (especially those expressing CLDN6). The humanized antibody of the present invention not only retains the functions and properties of the parent antibody, but also has a high degree of humanization, so that it can be safely administered to human subjects without causing immunogenic reactions. In particular, the antibody of the present invention hardly binds to other proteins in the CLDN family (e.g., CLDN3 and CLDN4). Therefore, the antibody (especially humanized antibody) of the present invention has great clinical value.

Embodiments of the present invention will be described in detail below with reference to the drawings and examples, but those skilled in the art will understand that the following drawings and examples are only for illustrating the present invention, rather than limiting the scope of the present invention. Various objects and advantages of the present invention will become apparent to those skilled in the art from the accompanying drawings and the following detailed description of preferred embodiments.

BRIEF DESCRIPTION OF THE DRAWINGS

FIG. 1A: CHOS-hCLDN6; FIG. 1B: CHOS-CLDN3; FIG. 1C: CHOS-CLDN4; FIG. 1D: CHOS-CLDN9.

FIG. 2A: CHOS-hCLDN6; FIG. 2B: CHOS-CLDN3; FIG. 2C: CHOS-CLDN4; FIG. 2D: CHOS-CLDN9.

FIG. 3A: OV90; FIG. 3B: NEC8; FIG. 3C: NTERA2; FIG. 3D: Bewo.

FIG. 4A: OV90; FIG. 4B: NEC8; FIG. 4C: NTERA2; FIG. 4D: Bewo.

FIG. 6A: the binding result of 15H2 antibody with a hotspot mutant to NEC8; FIG. 6B: the binding result of 15H2 antibody with a hotspot mutant to Bewo; FIG. 6C: the binding result of 9H3 antibody with a hotspot mutant to NEC8; FIG. 6D: the binding result of 9H3 antibody with a hotspot mutant to Bewo.

SEQUENCE INFORMATION

Figure 1:
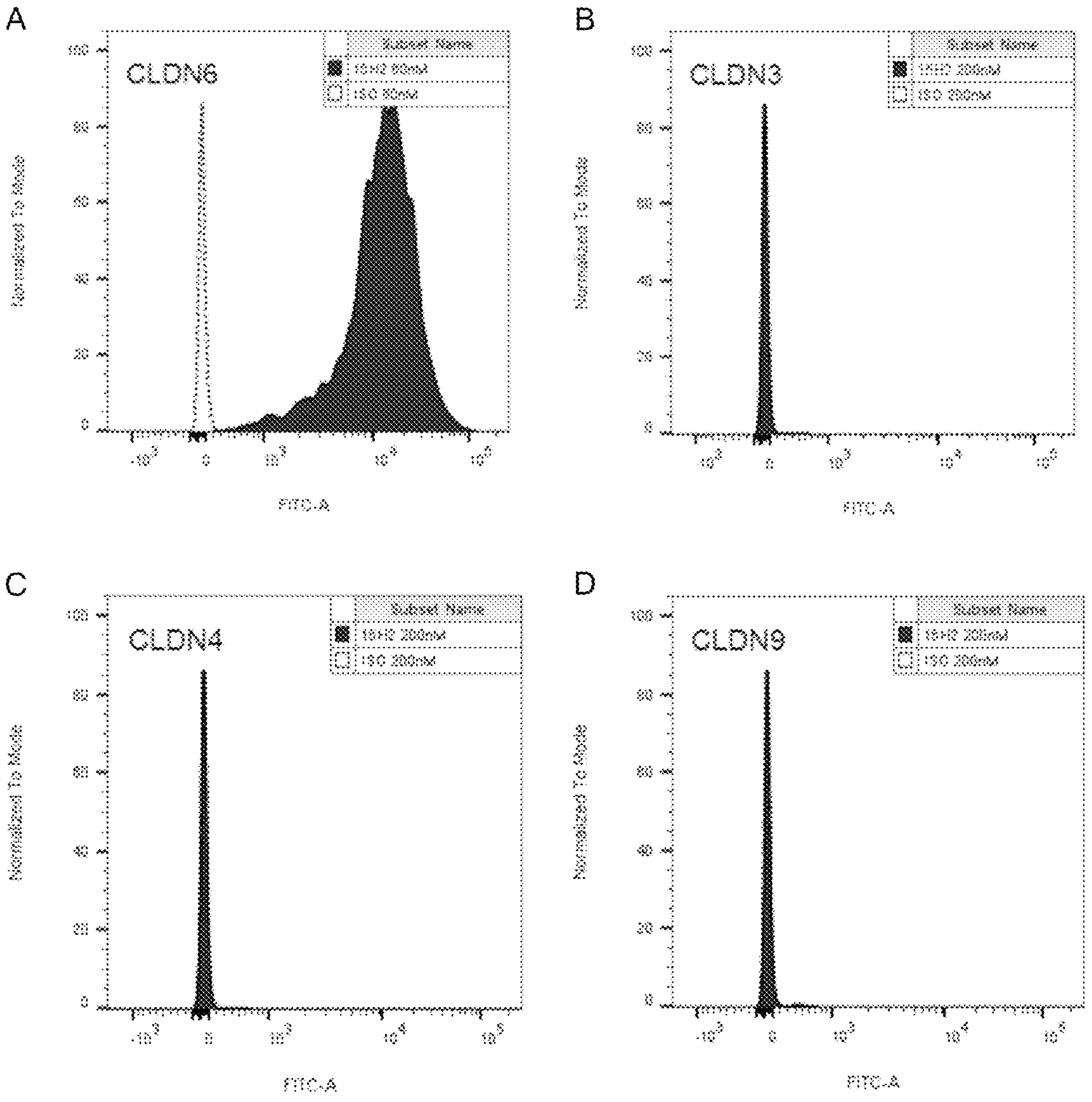
FIG. 1 shows the detection results of the binding activity of anti-CLDN6 murine antibody 15H2 to different cell surface CLDN proteins, respectively.

Information on some sequences involved in the present invention is provided in the table below.

| SEQ ID NO | Description | Sequence information |
|---|---|---|
| 1 | 15H2 heavy chain variable region | DVQLQESGPGLVKPSQSLSLTCSVTGYSITSGYYWNW IRQFPGNKLEWMGYISYDGSNNYNPSLKNRFSIIRDT SKNQFFLKFNSVTTEDTATYYCARGGYYFDYWGQGTT LTVSS |
| 2 | 15H2 light chain variable region | DIVMTQSPSSLAMSVGQKVTMSCKSSQSLLNTNNQKN YLAWYQQKPGQSPKLLVYFASTRESGVPDRFIGSGSG TDFTLTISSVQAEDLADYFCQQHYNAPRTFGGGTKLE IK |
| 3 | 15H2 HCDR1 | GYSITSGYY |
| 4 | 15H2 HCDR2 | ISYDGSN |
| 5 | 15H2 HCDR3 | ARGGYYFDY |
| 6 | 15H2 LCDR1 | QSLLNTNNQKNY |
| 7 | 15H2 LCDR2 | FASTRES |
| 8 | 15H2 LCDR3 | QQHYNAPRT |
| 9 | 7008-03 heavy chain variable region | EVQLVESGGGLVQPGGSLRLSCAASGFTFSIYGMSWV RQAPGKGLEWVATISRDASYTYFPDSVKGRFTISRDN AKNSLYLQMNSLRAEDTAVYYCVRLGDNDRGYAMDYW GQGTLVTVSS |
| 10 | 7008-03 light chain variable region | DVVMTQSPLSLPVTLGQPASISCRSSQSVVHVNANTY LEWYQQRPGQSPRLLIYKVSNRFPGVPDRFSGSGSGT DFTLKISRVEAEDVGVYYCFQGSHVPRTFGGGTKVEI K |
| 11 | 9H3 heavy chain variable region | EVQLVESGGDLVKPGGSLKLSCAASGFTFSIYGMSWV RQSPDRRLEWVATISRDGSYTYFPDSVKGRFTISRDN AKNTLYLQMSSLKSEDTAMYYCVRLGDNDRGYAMDYW GQGTSVTVSS |
| 12 | 9H3 light chain variable region | DVLMTQTPLSLPVSLGDQASISCRSSQSVVHVNGNTY LEWYLQKPGQSPRLLIYKVSNRFPGVPDRFSGSGSGT DFTLRISRVEAEDLGVYYCFQGSHVPRTFGGGTNLEI K |
| 13 | 9H3 HCDR1 | GFTFSIYG |
| 14 | 9H3 HCDR2 | ISRDGSYT |
| 15 | 9H3 HCDR3 | VRLGDNDRGYAMDY |
| 16 | 9H3 LCDR1 | QSVVHVNGNTY |
| 17 | 9H3 LCDR2 | KVSNRFP |
| 18 | 9H3 LCDR3 | FQGSHVPRT |
| 19 | 7008-01 heavy chain variable region | QVQLQESGPGLVKPSETLSLTCTVSGYSITSGYYWNW IRQPPGKGLEWMGYISYSGSNNYNPSLKNRVTISRDT SKNQFSLKLSSVTAADTAVYYCARGGYYFDYWGQGTL VTVSS |
| 20 | 7008-01 light chain variable region | DIVMTQSPDSLAVSLGERATINCKSSQSLLNTNNQKN YLAWYQQKPGQPPKLLIYFASTRESGVPDRFSGSGSG TDFTLTISSLQAEDVAVYFCQQHYNAPRTFGGGTKVE IK |
| 21 | Human IgG1 heavy chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPGK |
| 22 | Human k light chain constant region | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |

-continued

| SEQ ID NO | Description | Sequence information |
|---|---|---|
| 23 | 7008-03 HCDR2 | ISRDASYT |
| 24 | 7008-03 LCDR1 | QSVVHVNANTY |
| 25 | Nucleic acid sequence encoding 15H2 heavy chain variable region | GATGTACAGCTTCAGGAGTCAGGACCTGGCCTCGTGA AACCTTCTCAGTCTCTGTCTCTCACCTGCTCTGTCAC TGGCTACTCCATCACCAGTGGTTATTACTGGAACTGG ATCCGGCAGTTTCCAGGAAACAAACTGGAATGGATGG GCTACATAAGCTACGACGGTAGCAATAACTACAACCC ATCTCTCAAAAATCGATTCTCCATCATTCGTGACACA TCTAAGAACCAGTTTTTCCTGAAGTTCAATTCTGTGA CTACTGAGGACACAGCTACATATTACTGCGCCAGGGG GGGGTACTACTTTGACTACTGGGGCCAAGGCACCACT CTCACAGTCTCCTCA |
| 26 | Nucleic acid sequence encoding 15H2 light chain variable region | GACATTGTGATGACACAGTCTCCATCCTCCCTGGCTA TGTCAGTAGGACAGAAGGTCACTATGAGCTGCAAGTC CAGTCAGAGCCTTTTAAATACTAACAATCAAAAGAAC TATTTGGCCTGGTACCAGCAGAAACCAGGACAGTCTC CTAAACTTCTGGTATACTTTGCATCCACTAGGGAGTC TGGGGTCCCTGATCGCTTCATAGGCAGTGGATCTGGG ACAGATTTCACTCTTACCATCAGCAGTGTGCAGGCTG AAGACCTGGCAGATTACTTCTGTCAACAACATTATAA CGCTCCTCGGACGTTCGGTGGAGGCACCAAGCTGGAA ATCAAA |
| 27 | Nucleic acid sequence encoding 9H3 heavy chain variable region | GAGGTGCAGCTGGTGGAATCTGGGGGAGACTTAGTGA AGCCTGGAGGGTCCCTGAAACTCTCCTGTGCAGCCTC TGGATTCACTTTCAGTATCTATGGCATGTCTTGGGTT CGCCAGAGTCCAGACAGGAGGCTGGAATGGGTCGCAA CCATTAGTCGTGATGGTAGTTACACCTACTTTCCAGA CAGTGTGAAGGGGCGATTCACCATCTCCAGAGACAAT GCCAAGAACACCCTGTATTTGCAAATGAGCAGTCTGA AGTCTGAGGACACAGCCATGTATTACTGTGTAAGACT GGGTGATAACGACAGGGGCTATGCTATGGACTACTGG GGTCAAGGAACTTCAGTCACCGTCTCCTCA |
| 28 | Nucleic acid sequence encoding 9H3 light chain variable region | GATGTTTTGATGACCCAAACTCCACTCTCCCTGCCTG TCAGTCTTGGAGATCAAGCCTCCATCTCTTGCAGATC TAGTCAGAGTGTTGTACATGTTAATGGAAACACCTAT TTAGAATGGTACCTGCAGAAACCAGGCCAGTCTCCAA GGCTCCTGATCTACAAAGTTTCCAACCGCTTTCCTGG GGTCCCAGACAGGTTCAGTGGCAGTGGATCAGGGACA GATTTCACACTCAGGATCAGCAGAGTGGAGGCTGAGG ATCTGGGAGTTTATTACTGCTTTCAAGGTTCACATGT TCCTCGGACGTTCGGTGGAGGCACCAACCTGGAAATC AAA |
| 29 | Nucleic acid sequence encoding 7008-01 heavy chain variable region | CAGGTGCAGCTGCAGGAGAGCGGCCCCGGACTGGTGA AGCCCTCAGAGACACTGAGCCTGACATGCACAGTGAG CGGCTACTCCATTACAAGCGGCTACTACTGGAACTGG ATCAGACAGCCCCCCGGCAAGGGCCTGGAATGGATGG GCTATATCTCCTACAGCGGCAGCAACAACTACAACCC CAGCCTGAAGAACAGGGTGACCATCTCTCGCGACACC TCCAAGAACCAGTTCTCCCTGAAGCTGAGTAGCGTGA CTGCCGCTGACACCGCCGTGTACTATTGCGCCAGAGG CGGCTACTACTTCGACTACTGGGGCCAGGGCACCCTG GTGACCGTGAGCAGC |
| 30 | Nucleic acid sequence encoding 7008-01 light chain variable region | GACATTGTGATGACCCAGAGCCCCGACTCCCTGGCCG TGAGCCTGGGAGAAAGAGCCACCATCAACTGCAAGAG CAGCCAGAGCCTGCTGAACACCAACAACCAGAAAAAC TACCTGGCCTGGTACCAGCAGAAACCCGGCCAGCCCC CCAAACTGCTGATCTACTTCGCCTCCACCCGCGAGTC CGGCGTGCCTGATAGATTCTCCGGCAGCGGCAGCGGC ACCGACTTCACCCTGACTATCAGCAGCCTGCAGGCTG AGGACGTGGCCGTGTACTTCTGCCAGCAGCATTACAA CGCTCCCAGAACCTTTGGAGGAGGCACCAAGGTGGAA ATCAAG |
| 31 | Nucleic acid sequence encoding 7008-03 heavy chain variable region | GAGGTGCAGCTGGTGGAGAGCGGGGGGGGACTGGTGC AGCCAGGAGGAAGCCTGAGACTGAGCTGTGCCGCCAG CGGGTTTACATTTAGCATTTATGGGATGTCCTGGGTG AGACAGGCCCCCGGAAAAGGACTGGAGTGGGTGGCTA |

-continued

| SEQ ID NO | Description | Sequence information |
|---|---|---|
| | | CTATCAGCAGAGACGCTAGCTACACCTACTTCCCCGA TTCCGTGAAGGGCAGATTCACAATCAGCAGAGATAAC GCTAAGAACAGCCTGTATCTGCAGATGAACAGCCTGC GGGCCGAGGACACAGCCGTGTATTACTGCGTGAGGCT GGGCGACAACGATAGAGGATACGCCATGGACTACTGG GGGCAGGGAACACTGGTGACCGTGAGCAGC |
| 32 | Nucleic acid sequence encoding 7008-03 light chain variable region | GACGTGGTGATGACCCAGAGCCCCCTGAGCCTGCCCG TGACCCTGGGACAGCCCGCTAGTATCAGCTGCAGAAG CAGCCAGAGCGTGGTGCACGTGAACGCCAACACATAT CTGGAGTGGTATCAGCAGAGGCCTGGACAGAGCCCCA GACTGCTGATCTACAAGGTGAGCAACAGATTCCCAGG CGTGCCAGACAGATTCTCTGGAAGCGGCAGCGGAACA GACTTTACCCTGAAGATCTCCAGAGTGGAGGCCGAGG ACGTGGGAGTGTACTACTGCTTCCAGGGCAGCCACGT GCCCAGAACATTCGGCGGCGGCACCAAAGTGGAGATC AAA |
| 33 | 7008-01 HCDR2 | ISYSGSN |

Specific Models for Carrying Out the Present Invention

The present invention will now be described with reference to the following examples, which are intended to illustrate the present invention, but not to limit it.

Unless otherwise specified, the molecular biology experiment methods and immunoassay methods used in the present invention were basically referred to the methods described by J. Sambrook et al., Molecular Cloning: A Laboratory Manual, 2nd Edition, Cold Spring Harbor Laboratory Press, 1989, and F. M. Ausubel et al., Molecular Biology Experimental Guide, 3rd Edition, John Wiley & Sons, Inc., 1995; the restriction enzymes were used in accordance with the conditions recommended by the product manufacturer. Those skilled in the art understand that the examples describe the present invention by way of example and are not intended to limit the scope of the claimed invention.

Example 1: Production of Anti-CLDN6 Murine Antibody

Human CLDN6 (hCLDN6) or mouse CLDN6 (mCLDN6), or human CLDN3 (CLDN3), or human CLDN4 (CLDN4), or human CLDN9 (CLDN9) were over-expressed in HEK293 cells (ATCC) and CHOS cells (Invitrogen) by the method of lentiviral infection (MOI=3-10, 5 μg/ml polybrene), respectively. The lentivirus was provided by Shanghai Genechem Co., Ltd. After 72 hours of infection, the cells were cultured for 2 to 4 weeks with corresponding antibiotics, amplified and frozen to obtain a total of 9 cell lines, HEK293-hCLDN6, HKE293-mCLDN6, HEK293-CLDN3, HEK293-CLDN4, HEK293-CLDN9, CHOS-hCLDN6, CHOS-CLDN3, CHOS-CLDN4, and CHOS-CLDN9, which were used for subsequent experiments.

In order to obtain anti-human CLDN6 antibody, the constructed CHOS-hCLDN6 cells overexpressing human CLDN6 were used to immunize Balb/c mice (Beijing Vital River Laboratory Animal Technology Co., Ltd., strain code: 216); the adjuvant for primary immunization was complete Freund's adjuvant CFA (InvivoGen Company, Art. No.: vac-cfa-60), and the immune adjuvants used thereafter were all IFA (InvivoGen Company, Art. No.: vac-ifa-60); the immunization route was multi-point subcutaneous. After multiple immunizations, the splenocytes of immunized mice were fused with mouse myeloma cells SP2/0 using the polyethylene glycol method to obtain B cell fusions that could express antibodies and proliferate infinitely in vitro, which were cultured in HAT selective culture medium. The fused hybridoma cells were plated in a 96-well cell culture plate, and by detecting the ability of antibodies in supernatant to bind CLDN3/4/6/9 at cell level, the positive clones of interest (antibodies capable of binding to CLDN6, not binding to CLDN3/4/9; antibodies capable of binding to CLDN6/9 at the same time, but not binding to CLDN3/4) were screened out for 2-3 rounds of subcloning.

High-throughput screening for level of mouse antibody binding to cells: In the screening, the cells expressing human CLDN3/4/6/9 (CHOS-hCLDN6, CHOS-CLDN3, CHOS-CLDN4, CHOS-CLDN9) were plated separately. 10,000 cells were diluted in 100 μL of complete medium, by using a flat-bottom 96-well plate, the cells were adhered to wall or sunk to bottom of the well overnight, and the supernatant was discarded on the next day. 100 μL of hybridoma supernatant to be screened was added to the cell plate and incubated at room temperature for 1 hour. After the supernatant was removed, 100 μL of secondary antibody (DyLight488 goat anti-mouse IgG (Abcam, Cat. No.: ab97015) was added to each well, the concentration was 5 μg/mL, and incubation was carried out at room temperature for 0.5 hours. After the staining was completed, the supernatant was discarded, and 100 μL of DPBS was added to each well. The plate was loaded on machine for reading. A full-field cell scanning analyzer (Nexcelom, model Celigo® Image Cytometer) was used to measure and read the experimental plate. During the measurement, the fluorescent channel corresponding to the second antibody and the bright field channel were selected simultaneously to perform high-speed scanning imaging of the cells in the well. For the imaging obtained by the fluorescent channel, the cells bound to the antibody were counted according to the setting parameters of the fluorescently labeled cell morphology and the fluorescence intensity, while for the imaging obtained by the bright field channel, the adherent cells were counted according to the setting parameters of the cell morphology, and then the two sets of data were divided to obtain the percentage rate of the cells that were bound to the antibody and exhibited fluorescence accounting for the total number of cells. According to this rate, the binding effect of the antibody in the fusion tumor supernatant to the cells expressing CLDN3/4/6/9 was determined.

Flow cytometric evaluation of mouse antibody binding to CLDN3/4/6/9: 500,000 CLDN6 expressing cells (CHOS-hCLDN6, CHOS-CLDN3, CHOS-CLDN4, CHOS-CLDN9) were placed in FACS buffer (PBS+2% FBS)/well, added with the mouse antibody to be tested and incubated at 4° C. for 1 hour. The supernatant was removed by centrifugation, washing was performed twice with FACS buffer, secondary antibody (DyLight488 goat anti-mouse IgG, Abcam, Cat. No.: ab97015) was added and incubated at 4° C. for 0.5 hours. After staining, the supernatant was removed by centrifugation, washing was performed twice with FACS buffer, the cells were resuspended with FACS buffer, and then loaded on the machine for reading. A flow cytometer (BD company, model CantoII) was used to measure and read the experimental cells. During the measurement, the cell position was first delineated according to FCS and SSC, and then the fluorescence channel corresponding to the second antibody and SSC were selected to analyze the cells.

Figure 2:
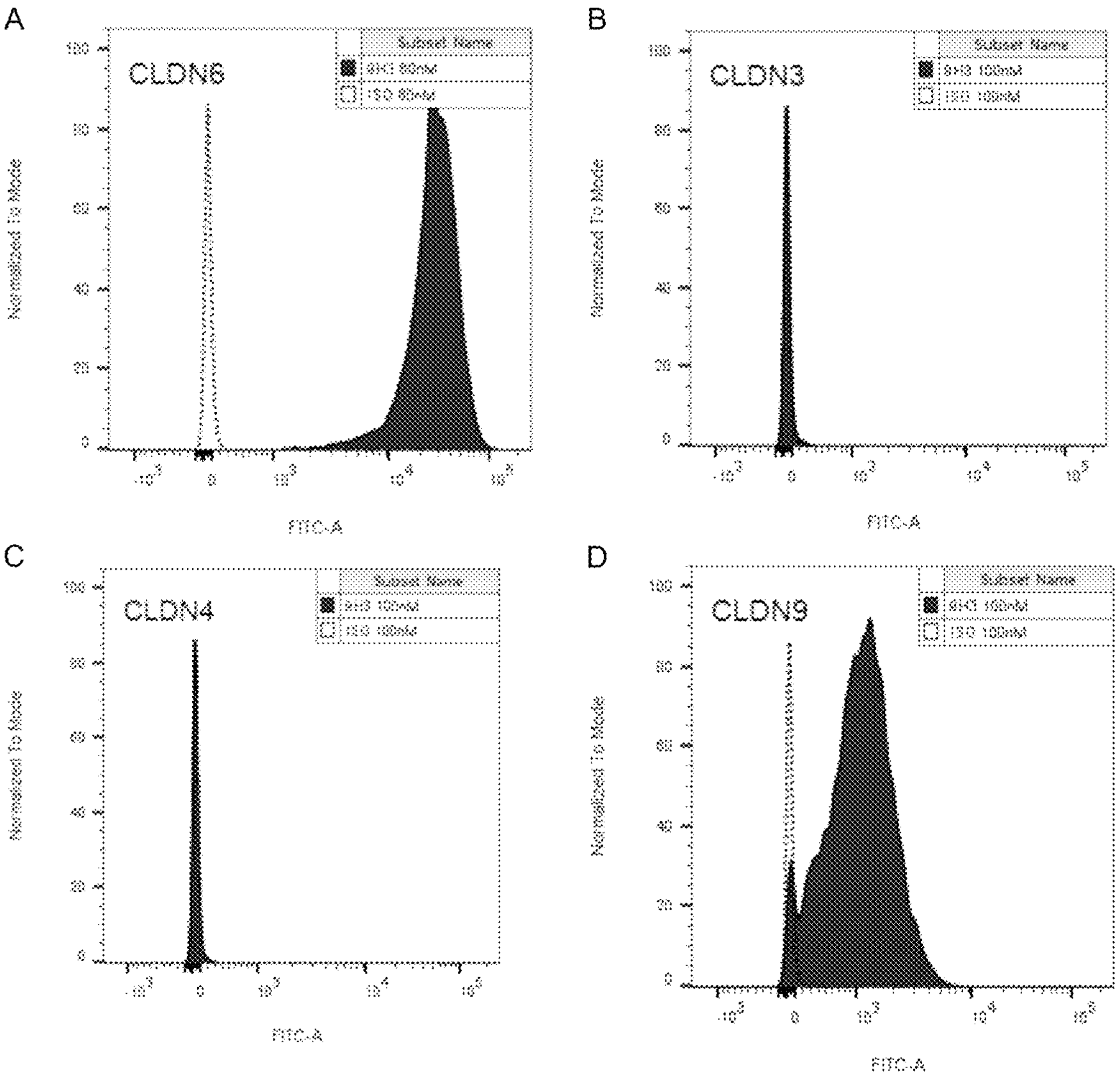
FIG. 2 shows the detection results of the binding activity of anti-CLDN6 murine antibody 9H3 to different cell surface CLDN proteins, respectively.

The results of murine antibody 15H2 binding to CHOS-hCLDN6, CHOS-CLDN3, CHOS-CLDN4, and CHOS-CLDN9 were shown in FIG. 1. As shown in the figure, the isotype control antibody ISO (Beyotime, CatA7028) did not bind to CHOS-hCLDN6, CHOS-CLDN3, CHOS-CLDN4, CHOS-CLDN9 cells, while the antibody 15H2 was able to bind to CHOS-hCLDN6 cells, but hardly bound to CHOS-CLDN3, CHOS-CLDN4 and CHOS-CLDN9 cells; the results of murine antibody 9H3 binding to CHOS-hCLDN6, CHOS-CLDN3, CHOS-CLDN4, and CHOS-CLDN9 were shown in FIG. 2. As shown in the figure, the isotype control antibody ISO did not bind to CHOS-hCLDN6, CHOS-CLDN3, CHOS-CLDN4, CHOS-CLDN9 cells, while the antibody 9H3 was able to bind to CHOS-hCLDN6 and CHOS-CLDN9 cells, but barely bound to CHOS-CLDN3 and CHOS-CLDN4 cells.

Example 2: Determination of Variable Region Sequence of Anti-CLDN6 Murine Antibody Hybridoma cells were collected by centrifugation, added with 1 ml of TRIzol and 0.2 ml of chloroform for every 5~10×10$^6$ cells, shaken vigorously for 15 seconds, allowed to stand at room temperature for 3 minutes, the aqueous phase was taken by centrifugation and added with 0.5 ml of isopropanol, allowed to stand for 10 minutes at room temperature, then the precipitate was collected, washed with ethanol, then dried to obtain RNA. Template RNA and primers were added into a cooled centrifuge tube in ice-bath, after the primers and templates paired correctly, the reverse transcription process was carried out, and then PCR amplification was carried out. 2.5 µl of dNTP/ddNTP mixture was added into each of four microcentrifuge tubes, and the mixture was incubated at 37° C. for 5 minutes for later use. 1 pmol of PCR-amplified double-stranded DNA, 10 pmol of sequencing primers, 2 µl of 5× sequencing buffer were added to an empty microcentrifuge tube, and double-distilled water was added to reach a total volume of 10 µl, heated at 96° C. for 8 minutes, then cooled in an ice-bath for 1 minute, and centrifuged at 4° C. and 10000 g for 10 seconds. 2 µl of pre-cooled labeling mixture (dCTP, dGTP, dTTP, each 0.75 µmol/L), 1 µl of 0.1 mol/L DDT, 2 U sequence enzyme were added, and water was added to reach 15 µl, mixed well and placed on ice for 2 min to label the newly synthesized DNA strand. 3.5 µl of labeling reaction mixture was added into 4 prepared microcentrifuge tubes and incubated at 37° C. for 5 min, then 4 µl of stop solution was added to each tube. The samples were thermally denatured in a water bath at 80° C. for 5 minutes, then added to the sequencing gel, 2 µl for each lane, and the fragments were separated by electrophoresis to collect sequence information.

The VH and VL sequences of the two murine antibodies were shown in Table 1. Furthermore, the CDR sequences of the two murine monoclonal antibodies were determined by the IMGT numbering system.

TABLE 1

Sequence information of murine antibodies

| | SEQ ID NO: | | | | | | | |
|---|---|---|---|---|---|---|---|---|
| Antibody | VH | VHCDR1 | VHCDR2 | VHCDR3 | VL | VLCDR1 | VLCDR2 | VLCDR3 |
| 15H2 | 1 | 3 | 4 | 5 | 2 | 6 | 7 | 8 |
| 9H3 | 11 | 13 | 14 | 15 | 12 | 16 | 17 | 18 |

Example 3: Recombinant Expression of Chimeric Anti-CLDN6 Antibody

After the antibody gene sequence was verified, the variable regions of the mouse antibody were linked to the constant regions of the human antibody (human IgG1), and the expression plasmid containing the antibody gene was transfected into mammalian cells. The supernatant of culture flask-grown mammalian cells containing antibody clone was harvested, purified with a protein A column, and the antibody protein was eluted using 100 mM acetic acid at pH 3.0. The purified antibody protein was then loaded onto a size exclusion chromatography column for further separation and purification. The antibody proteins corresponding to monomers were formulated in PBS buffer supplemented with 20% glycerol.

Example 4: Humanization and Post-Translational Modification Hotspot Mutation of Mouse Anti-Human CLDN6 Antibody In order to increase the sequence homology between the candidate antibody and the human antibody and reduce the immunogenicity of the antibody to human, the murine antibody provided in the above examples could be designed and prepared for humanization, and murine CDR regions could be inserted into human framework sequences using methods known in the art (see, Winter, U.S. Pat. No. 5,225,539; Queen et al., U.S. Pat. Nos. 5,530,101; 5,585,089; 5,693,762 and 6,180,370; and Lo, Benny, K. C., editor, in Antibody Engineering: Methods and Protocols, volume 248, Humana Press, New Jersey, 2004).

Specifically, the heavy chain and light chain CDR regions of murine antibodies 15H2 and 9H3 were respectively constructed on the FR frameworks of the corresponding humanized template, and a series of back mutations of the amino acid residues in the FR region of the humanized template were carried out, so that the humanized antibody retained the antigen-binding ability of the murine antibody as much as possible.

Figure 6:
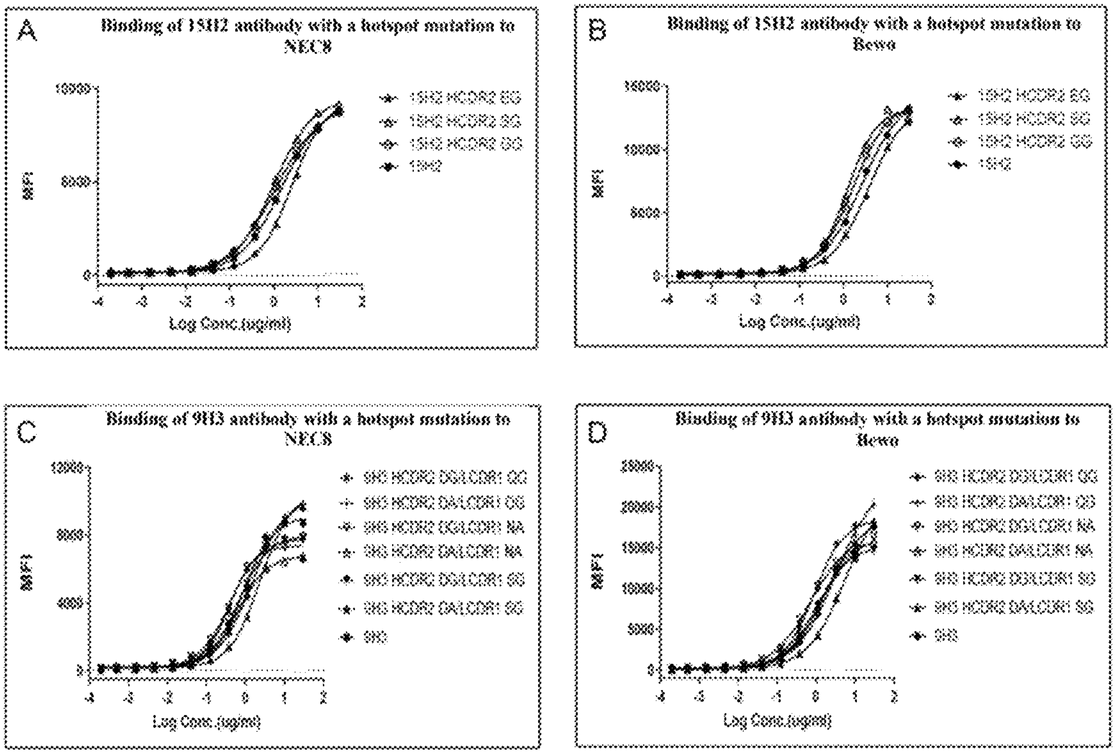
FIG. 6 shows the binding results of antibodies with a hotspot mutant to different CLDN6-expressing tumor cells, respectively.

At the same time, in view of the possible post-translational modification hotspots (PTM hotspot) in the CDR region of the murine antibodies, for example, aspartate isomerization hotspot DG in 15H2 HCDR2, aspartate isomerization hotspot DG in 9H3 HCDR2, deamination hotspot NG in 9H3 LCDR1, these hotspots were mutated by methods known in the art. For example, D in the aspartate isomerization hotspot DG was mutated to E/S/G, etc., or G in DG was mutated to A/S/D, etc., or N in deamination hotsport NG was mutated to Q/S/A, etc., or G in NG was mutated to A/S/D, etc. It had been verified by experiments that most of the mutations mentioned above did not change the ability of the antibodies to bind to CLDN6-expressing cells (e.g., 15H2 HCDR2 DG was mutated to EG/SG/GG; 9H3 LCDR1 NG was mutated to QG/NA/SG; 9H3 LCDR1 NG was mutated to QG and its HCDR2 DG was mutated to DA at the same time), or changed within 3 times (9H3 LCDR1 NG was mutated to NA and its HCDR2 DG was mutated to DA at the same time; 9H3 LCDR1 NG was mutated to SG and its HCDR2 DG was mutated to DA at the same time). FIGS. 6A and 6B showed the results of some hotspot mutation antibodies of 15H2 binding to the CLDN6-expressing tumor cell NEC8/Bewo, and FIGS. 6C and 6D showed the results of some hotspot mutation antibodies of 9H3 binding to the CLDN6-expressing tumor cell NEC8/Bewo.

According to the above method, the inventors prepared a series of humanized hotspot mutant antibodies of murine antibody 15H2 and murine antibody 9H3, and after screening for the ability to bind to CLDN6-expressing cells, it was preferred that for each mouse antibody, there were one humanized antibody and one hotspot mutation antibody, named 7008-01 (its heavy chain variable region and light chain variable region were set forth in SEQ ID NO: 19 and 20, respectively) and 7008-03 (its heavy chain variable region and light chain variable region were set forth in SEQ ID NO: 9 and 10, respectively). For each antibody, the heavy chain constant region was set forth in SEQ ID NO: 21, and the light chain constant region was set forth in SEQ ID NO: 22.

Example 5: Evaluation of Antigen-Binding Activity of Humanized Anti-CLDN6 Antibody 500,000 CLDN6-naturally expressing tumor cells (0V90, ATCC; NEC8, JCRB; NTERA2, Nanjing Cobioer Biosciences Co., Ltd; Bewo, Nanjing Cobioer Biosciences Co., Ltd) were placed in FACS buffer for later use, in which round-bottom low-adsorption 96-well plates were used. Antibody samples were serially diluted with FACS buffer. The diluted antibody was added to the cell plates, and FACS buffer was added to the corresponding negative control wells, and incubation was performed at 4° C. for 1 hour. After centrifuging to remove the supernatant, washing was performed twice with FACS buffer, then secondary antibody (DyLight488 goat anti-human IgG, Abcam, Cat. No.: ab97003) was added to each well and incubated at 4° C. for 0.5 hour. After staining, the supernatant was removed by centrifugation, washing was performed twice with FACS buffer, and the cells were resuspended by adding FACS buffer to each well, and then loaded on a machine for reading. A flow cytometer (BD Company, model CantoII) was used to measure and read the cells in the experimental plate. During the measurement, the position of cells was first delineated according to FCS and SSC, and then the fluorescence channel corresponding to the second antibody and SSC were selected to analyze the cells. GraphPad was used for data analysis, the logarithm of antibody concentration was used on the abscissa, and the average fluorescence intensity value was used on the ordinate. According to the curve, the EC50 of anti-CLDN6 antibody was fitted.

Figure 3:
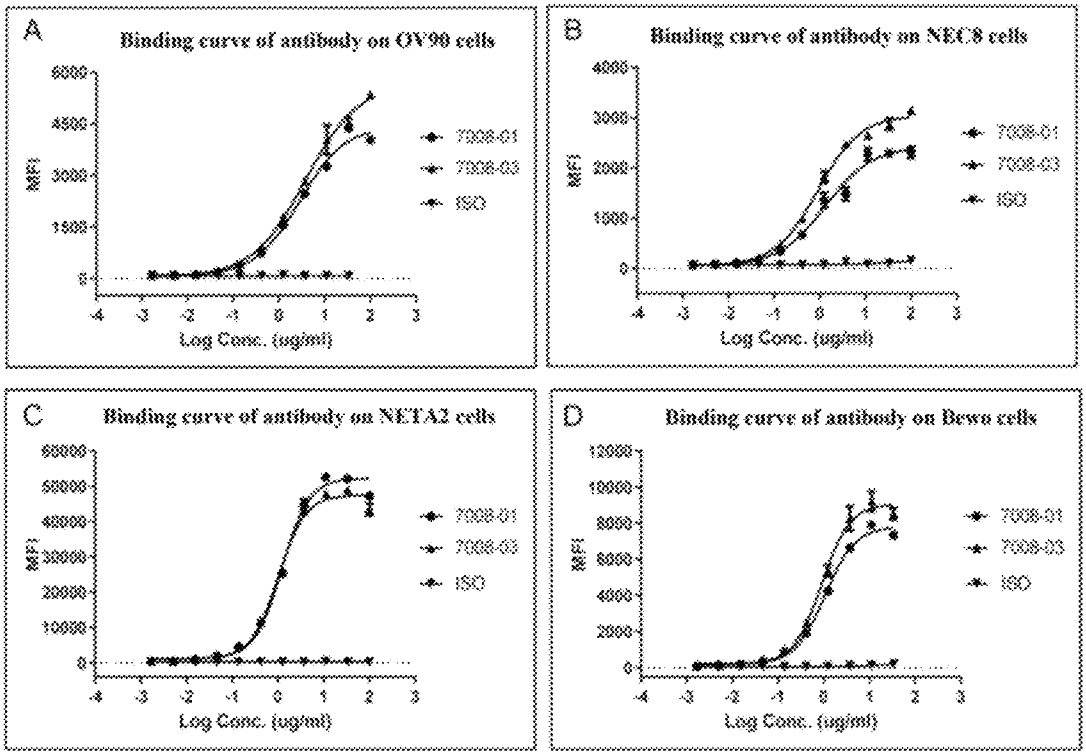
FIG. 3 shows the binding results of humanized antibodies 7008-01 and 7008-03 to four tumor cells naturally expressing human CLDN6.

The results of the humanized antibodies 7008-01 and 7008-03 binding to four tumor cells naturally expressing human CLDN6 (0V90/NEC8/NTERA2/Bewo) were shown in FIG. 3. Table 2 showed the EC50 and maximum binding value (Top MFI) of the two antibodies binding to the tumor cells. The results showed that humanized antibodies 7008-01 and 7008-03 had good binding activity to membrane surface CLDN6.

TABLE 2

Results of antibodies binding to CLDN6-positive tumor cells

| | 7008-01 | | 7008-03 | |
|---|---|---|---|---|
| | EC50 (ug/mL) | Top MFI | EC50 (ug/mL) | Top MFI |
| OV90 | 2.85 | 4438 | 3.79 | 5692 |
| NEC8 | 1.31 | 2427 | 0.91 | 3046 |
| NTERA2 | 1.22 | 52326 | 1.02 | 47527 |
| Bewo | 1.06 | 7815 | 0.90 | 9069 |

Example 6: Effect of Antibody-Induced ADCC (Antibody Dependent Cellular Cytotoxicity)

CLDN6-naturally expressing tumor cells (0V90, ATCC; NEC8, JCRB; NTERA2, Nanjing Kebai Bio; Bewo, Nanjing Kebai Bio) were used as target cells, and Jurkat-NFAT-Luc-CD16 cell line with in-house constructed and stably transfected CD16 receptor and NFAT (Nuclear Factor of Activated T-cells) reaction element was used as effector cell. The experiment was carried out in 96-well flat bottom cell plates (Corning 3903). Serially diluted antibodies were added to the target cells and incubated at 37° C. for 30 minutes. 60,000 effector cells were added for every 10,000 target cells, and reacted at 37° C. for 4-6 hours. After the reaction, One-Glo™ reagent (Promega, E6110) was added for fluorescence color development, and a Tecan Spark10 microplate reader was used to measure the luminescence values of the cell plates. GraphPad was used for data analysis, the logarithm of the antibody concentration was used on the abscissa, and the luminescence value of the corresponding well was used on the ordinate, and the EC50 of the antibody-dependent cytotoxicity of the anti-CLDN6 antibody was calculated according to the curve fitting.

Figure 4:
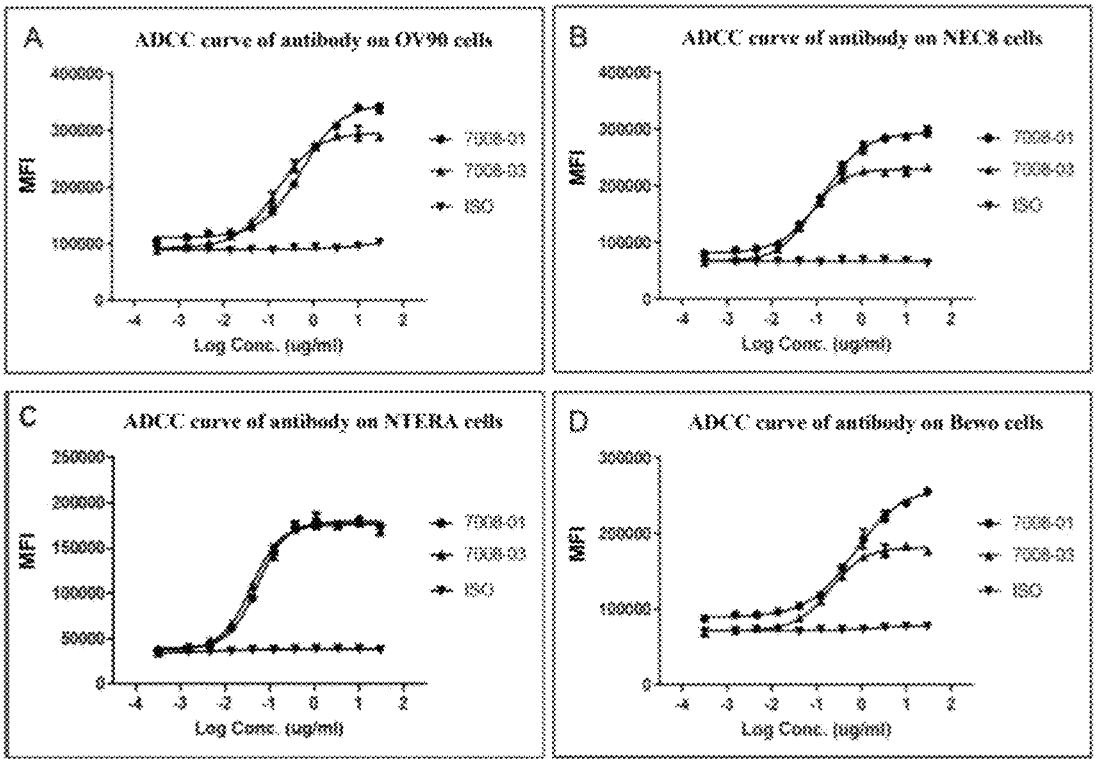
FIG. 4 shows the results of antibody-dependent cytotoxicity of effector cells induced by humanized antibodies 7008-01 and 7008-03 on four tumor cells naturally expressing human CLDN6.

The humanized antibodies 7008-01 and 7008-03 induced antibody-dependent cytotoxicity of effector cells on the four human CLDN6-naturally expressing tumor cells (0V90/NEC8/NTERA2/Bewo) were shown in FIG. 4. Table 3 showed the EC50 values and the maximum values (Top Lum) of the two antibodies in ADCC of different tumor cells. The results showed that both the humanized antibodies 7008-01 and 7008-03 could effectively induce effector cells to kill tumor cells expressing CLDN6.

TABLE 3

| ADCC effect of antibodies on CLDN6-positive tumor cells | | | | |
|---|---|---|---|---|
| | 7008-01 | | 7008-03 | |
| | EC50 (ug/mL) | Top Lum | EC50 (ug/mL) | Top Lum |
| OV90 | 0.55 | 346241 | 0.16 | 295296 |
| NEC8 | 0.15 | 29400 | 0.071 | 229365 |
| NTERA2 | 0.55 | 179190 | 0.40 | 176043 |
| Bewo | 0.70 | 259125 | 0.21 | 181171 |

Example 7: Antibody-Induced CDC (Complement Dependent Cytotoxicity) Effect

CLDN6-naturally expressing tumor cells NTERA2 were used as target cells. The target cells were pre-mixed with the BATDA fluorescence-enhanced ligand reagent (PerkinElmer, AD0116) in the EuTDA cytotoxicity detection kit at a ratio of $1\times10^6$ cells per ml, and incubated at 37° C. for 20 minutes; the treated target cells ($5\times10^3$) were mixed with antibodies of various concentrations and human serum (TPCS, A515) as a source of complement at a ratio of 1:8, and incubated in a 96-well round bottom plate (Coring, GLS3799) at 37° C. for 3 hours. After the incubation, the supernatant in the 96-well round-bottom plate was transferred to a 96-well flat-bottom plate (Coring, Cat. No. 3903) added with europium solution (PerkinElmer, AD0116) and further incubated at room temperature for 15 minutes. A multifunctional microplate reader was used to measure the emission light emitted from a receptor after an energy excited a fluorescent donor released into the supernatant after cell death in each well and then transferred to the receptor (excitation: 320/340 nm, emission: 615 nm).

Cytotoxicity was calculated using the following formula: Cytotoxicity percentage=100×[1−(Max−data)/(Max−Min)]

wherein, Data was the value of the experiment (cells were incubated with antibody and complement), Min was the minimum cytotoxicity, i.e., the background value of the experiment (cells were incubated with medium and complement), and Max was the maximum cytotoxicity (cells were incubated with lysate and complement). GraphPad was used for data analysis, the logarithm of the antibody concentration was used on the abscissa, and the fluorescence values of the corresponding wells were used on the ordinate, and the EC50 of the complement-dependent cytotoxicity effect of the anti-CLDN6 antibody was calculated according to the curve fitting.

Figure 5:
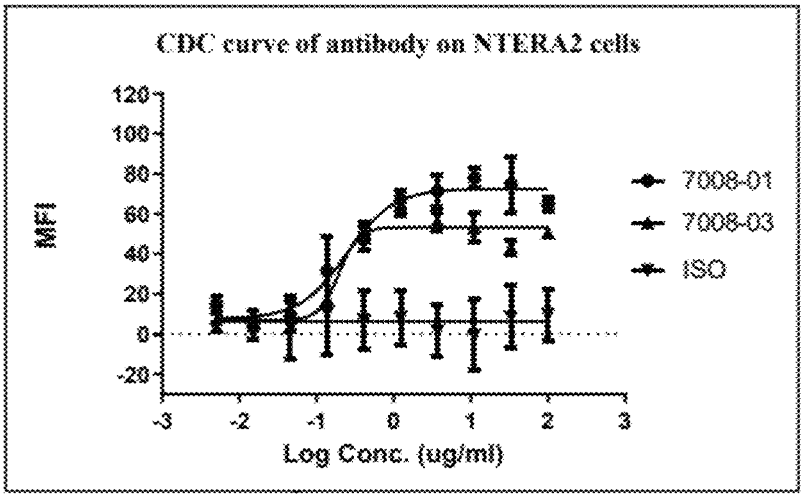
FIG. 5 shows the results of complement-dependent cytotoxic effect of complements induced by humanized antibodies 7008-01 and 7008-03 on NTERA2 tumor cells naturally expressing human CLDN6.

The humanized antibodies 7008-01 and 7008-03 induced complement-dependent cytotoxicity effect of complement on human CLDN6-naturally expressing NTERA2 tumor cells were shown in FIG. 5. The results showed that both humanized antibodies 7008-01 and 7008-03 could effectively induce complement to kill tumor cells expressing CLDN6.

Example 8: CLDN6 Internalization Mediated by Anti-CLDN6 Antibody

In this example, anti-CLDN6 antibody-mediated internalization of CLDN6 was tested by flow cytometry. To measure the relationship between the internalization caused by the antibody and time, CLDN6-naturally expressing tumor cells (0V90/Bewo) were incubated with 10 μg/mL antibody for different time at 37° C./4° C. After washing was performed for several times with PBS containing 2% FBS, 10 μg/mL secondary antibody was added for staining at 4° C. for 30 minutes, and then the expression of CLDN6 in the cells was analyzed by flow cytometry.

MFI37 was the MFI of the sample incubated at 37° C.; MFI4 was the MFI of the sample incubated at 4° C., under which only binding occurred but not endocytosis. The MFI background was the MFI of the second antibody only. The percentage of the antibody-mediated cell surface CLDN6 endocytosis was calculated by the following formula:

Percentage of internalized CLDN6=100−100×($MFI4$−$MFI37$)/$MFI4$

The results were shown in Table 4. The humanized antibodies 7008-01 and 7008-03 mediated the internalization of CLDN6 on the surface of tumor cells to varying degrees.

TABLE 4

| Antibody-mediated CLDN6 internalization rates on tumor cell surface (%) | | | | | | | | |
|---|---|---|---|---|---|---|---|---|
| Cell | Antibody | 4 hours | 2.5 hours | 2 hours | 1.5 hours | 1 hour | 0.5 hours | 0 hours |
| OV90 | 7008-01 | 6.2 | — | 12.8 | — | 9.1 | 8.5 | 0.0 |
| | 7008-03 | 22.0 | 9.3 | — | −0.1 | −3.1 | — | 0.0 |
| Bewo | 7008-01 | 2.6 | — | 4.3 | — | 4.0 | 1.6 | 0.0 |
| | 7008-03 | 20.0 | 12.3 | — | 10.0 | 3.9 | — | 0.0 |

Although the specific models for carrying out the present invention have been described in detail, those skilled in the art will understand that: according to all the teachings that have been published, various modifications and changes can be made to the details, and these changes are all within the protection scope of the present invention. The full scope of the present invention is given by the claims appended hereto and any equivalents thereof.

What is claimed is:

1. An antibody or antigen-binding fragment thereof selected from the group consisting of:

(1) an antibody or antigen-binding fragment thereof comprising a heavy chain variable region (VH) comprising a VH complementarity determining region (CDR) 1 having the sequence as set forth in SEQ ID NO: 3, a VH CDR2 having the sequence as set forth in SEQ ID NO: 4, and a VH CDR3 having the sequence as set forth in SEQ ID NO: 5; and a light chain variable region (VL) comprising a VL CDR1 having the sequence as set forth in SEQ ID NO: 6, a VL CDR2 having the sequence as set forth in SEQ ID NO: 7, and a VL CDR3 having the sequence as set forth in SEQ ID NO: 8;

(2) an antibody or antigen-binding fragment thereof comprising a VH comprising a VH CDR 1 having the sequence as set forth in SEQ ID NO: 3, a VH CDR2 having the sequence as set forth in SEQ ID NO: 33, and a VH CDR3 having the sequence as set forth in SEQ ID NO: 5; and a VL comprising a VL CDR1 having the sequence as set forth in SEQ ID NO: 6, a VL CDR2 having the sequence as set forth in SEQ ID NO: 7, and a VL CDR3 having the sequence as set forth in SEQ ID NO: 8;

(3) an antibody or antigen-binding fragment thereof comprising a VH comprising the a VH CDR1 having the sequence as set forth in SEQ ID NO: 13, a VH CDR2 having the sequence as set forth in SEQ ID NO: 14, and a VH CDR3 having the sequence as set forth in SEQ ID NO: 15; and a VL comprising a VL CDR1 having the sequence as set forth in SEQ ID NO: 16, a VL CDR2 having the sequence as set forth in SEQ ID NO: 17, and a VL CDR3 having the sequence as set forth in SEQ ID NO: 18; and (4) an antibody or antigen-binding fragment thereof comprising a VH comprising a VH CDR1 having the sequence as set forth in SEQ ID NO: 13, a VH CDR2 having the sequence as set forth in SEQ ID NO: 23, and a VH CDR3 having the sequence as set forth in SEQ ID NO: 15; and a VL comprising a VL CDR1 having the sequence as set forth in SEQ ID NO: 24, a VL CDR2 having the sequence as set forth in SEQ ID NO: 17, and a VL CDR3 having the sequence as set forth in SEQ ID NO: 18.

2. The antibody or antigen-binding fragment thereof according to claim 1, wherein the antibody or antigen-binding fragment thereof further comprises one or more of:

(1) a human-derived framework region (FR) sequence;

(2) an FR sequence of a human immunoglobulin; and (3) an FR sequence of human rearranged antibody sequences or human germline antibody sequences.

3. The antibody or antigen-binding fragment thereof according to claim 1, wherein the antibody or antigen-binding fragment thereof comprises:

(1) a VH having the sequence as set forth in SEQ ID NO: 1 and a VL having the sequence as set forth in SEQ ID NO: 2;

(2) a VH having the sequence as set forth in SEQ ID NO: 19 and a VL having the sequence as set forth in SEQ ID NO: 20;

(3) a VH having the sequence as set forth in SEQ ID NO: 11 and a VL having the sequence as set forth in SEQ ID NO: 12; or (4) a VH having the sequence as set forth in SEQ ID NO: 9 and a VL having the sequence as set forth in SEQ ID NO: 10.

4. The antibody or antigen-binding fragment thereof according to claim 1, wherein the antibody or antigen-binding fragment thereof further comprises: a heavy chain constant region (CH) of a human immunoglobulin or variant thereof and a light chain constant region (CL) of a human immunoglobulin or variant thereof;

wherein, optionally, the antibody or antigen-binding fragment thereof further comprises one or more of:

(1) an IgG heavy chain constant region;

(2) a heavy chain constant region having the sequence as set forth in SEQ ID NO: 21;

(3) a k or λ light chain constant region;

(4) a light chain constant region having the sequence as shown in SEQ ID NO: 22; and (5) a label;

wherein, optionally, the antigen-binding fragment is selected from the group consisting of Fab, Fab', (Fab') 2, Fv, disulfide-bonded Fv, scFv, diabody and single domain antibody (sdAb);

and the antibody is a murine antibody, a chimeric antibody, a humanized antibody, a bispecific antibody and a multispecific antibody.

5. An isolated nucleic acid molecule, wherein the isolated nucleic acid molecule encodes the antibody or antigen-binding fragment thereof according to claim 1.

6. A vector comprising the isolated nucleic acid molecule according to claim 5.

7. A host cell comprising the isolated nucleic acid molecule according to claim 5 or a vector comprising the isolated nucleic acid molecule.

8. A method for preparing the antibody or antigen-binding fragment thereof according to claim 1, comprising: culturing a host cell comprising an isolated nucleic acid molecule encoding the antibody or antigen-binding fragment thereof under a condition that allows the expression of the antibody or antigen-binding fragment thereof, and recovering the antibody or antigen-binding fragment thereof from a culture of the cultured host cell.

9. A bispecific or multispecific molecule comprising the antibody or antigen-binding fragment thereof according to claim 1;

wherein, optionally, the bispecific or multispecific molecule is selected from one or more of:

(1) a bispecific or multispecific molecule that specifically binds to CLDN6 and additionally specifically binds to one or more other targets;

(2) a bispecific or multispecific molecule that further comprises at least one molecule having a second binding specificity for a second target; and (3) a bispecific or multispecific molecule that further comprises a second antibody.

10. An immunoconjugate comprising the antibody or antigen-binding fragment thereof according to claim 1 and a therapeutic agent conjugated to the antibody or antigen-binding fragment thereof;

wherein, optionally, the therapeutic agent is one or more of:

(1) a cytotoxic agent; or (2) selected from the group consisting of alkylating agents, mitosis inhibitors, antitumor antibiotics, antimetabolites, topoisomerase inhibitors, tyrosine kinase inhibitors, radionuclide agents, and any combination thereof; and wherein the immunoconjugate is an antibody-drug conjugate (ADC).

11. A pharmaceutical composition comprising (i) the antibody or antigen-binding fragment thereof according to claim 1, a bispecific or multispecific molecule comprising the antibody or antigen-binding fragment thereof, or an immunoconjugate comprising the antibody or antigen-binding fragment thereof, and (ii) one or more of a pharmaceutically acceptable carrier or excipient;

wherein, optionally, the pharmaceutical composition further comprises an additional pharmaceutically active agent;

wherein, optionally, the additional pharmaceutically active agent is one or more of:

(1) an agent with an antitumor activity; and (2) an alkylating agent, mitotic inhibitor, antitumor antibiotic, antimetabolite, topoisomerase inhibitor, tyrosine kinase inhibitor, radionuclide agent, radiosensitizer, anti-angiogenic agent, cytokine, molecularly targeted drug, immune checkpoint inhibitor or oncolytic virus; and wherein the antibody or antigen-binding fragment thereof, the bispecific or multispecific molecule, or the immunoconjugate, and the additional pharmaceutically active agent are provided as separate components or as components of the same composition.

12. A kit, comprising the antibody or antigen-binding fragment thereof according to claim 1; and, optionally, a second antibody; wherein one or more of the antibody or antigen-binding fragment thereof or the second antibody optionally comprises a detectable label.

13. A chimeric antigen receptor comprising an antigen-binding domain of the antibody or antigen-binding fragment thereof according to claim 1;

wherein, optionally, the antigen binding domain of the chimeric antigen receptor:

(1) comprises a heavy chain variable region and a light chain variable region of the antibody or antigen-binding fragment thereof according to claim 1; or (2) the antigen-binding domain is a scFv.

14. An isolated nucleic acid molecule, wherein the isolated nucleic acid molecule encodes the chimeric antigen receptor according to claim 13.

15. A vector, comprising the isolated nucleic acid molecule according to claim 14.

16. A host cell comprising the isolated nucleic acid molecule according to claim 14 or a vector comprising the isolated nucleic acid molecule; wherein optionally, the host cell is:

(1) an immune effector cell;

(2) a T cell or an NK cell; or (3) a chimeric antigen receptor T cell (CAR-T).

17. A method for reducing the expression of CLDN6 on the surface of a cell, the method comprising contacting a cell expressing CLDN6 on the surface thereof with one or more of:

(1) an antibody or antigen-binding fragment thereof according to claim 1, (2) a bispecific or multi specific molecule comprising an antibody or antigen-binding fragment thereof according to claim 1, (3) an immunoconjugate comprising an antibody or antigen-binding fragment thereof according to claim 1, (4) a pharmaceutical composition comprising an antibody or antigen-binding fragment thereof according to claim 1, (5) a chimeric antigen receptor comprising an antibody or antigen-binding fragment thereof according to claim 1, (6) a host cell comprising an isolated nucleic acid molecule encoding a chimeric antigen receptor comprising an antibody or antigen-binding fragment thereof according to claim 1, and (7) any combination thereof, so as to reduce expression of CLDN6 on the surface of the cell, wherein, optionally, the cell is a tumor cell expressing CLDN6 .

18. A method for inhibiting growth of, or killing, a tumor cell expressing CLDN6, comprising contacting the tumor cell with an effective amount of one or more of:

(1) an antibody or antigen-binding fragment thereof according to claim 1, (2) a bispecific or multispecific molecule comprising an antibody or antigen-binding fragment thereof according to claim 1, (3) an immunoconjugate comprising an antibody or antigen-binding fragment thereof according to claim 1, (4) a pharmaceutical composition comprising an antibody or antigen-binding fragment thereof according to claim 1, (5) a chimeric antigen receptor comprising an antibody or antigen-binding fragment thereof according to claim 1, (6) a host cell comprising an isolated nucleic acid molecule encoding a chimeric antigen receptor comprising an antibody or antigen-binding fragment thereof according to claim 1, and (7) any combination thereof.

19. A method for treating a tumor in a subject, the method comprising administering to a subject in need thereof an effective amount of one or more of:

(1) an antibody or antigen-binding fragment thereof according to claim 1, (2) a bispecific or multispecific molecule comprising an antibody or antigen-binding fragment thereof according to claim 1, (3) an immunoconjugate comprising an antibody or antigen-binding fragment thereof according to claim 1, (4) a pharmaceutical composition comprising an antibody or antigen-binding fragment thereof according to claim 1, (5) a chimeric antigen receptor comprising an antibody or antigen-binding fragment thereof according to claim 1, (6) a host cell comprising an isolated nucleic acid molecule encoding a chimeric antigen receptor comprising an antibody or antigen-binding fragment thereof according to claim 1; and (7) any combination thereof;

wherein, optionally, the tumor is characterized by one or both of:

(1) the tumor comprises one or more tumor cells expressing CLDN6; and (2) the tumor is selected from the group consisting of ovarian cancer, testicular cancer, gastric cancer, endometrial cancer, lung cancer, esophageal cancer, pancreatic cancer, bronchial cancer, breast cancer, ear nose throat (ENT) cancer, colon cancer, liver cancer, head and neck cancer, gallbladder cancer and metastasis thereof;

wherein, optionally, the subject is a mammal or a human, wherein, optionally, the method further comprises administering to the subject an additional pharmaceutical agent having anti-tumor activity;

wherein, optionally, the additional pharmaceutical agent having anti-tumor activity is an alkylating agent, a mitotic inhibitor, an anti-tumor antibiotic, an antimetabolite, a topoisomerase inhibitor, a tyrosine kinase inhibitor, a radionuclide, a radiosensitizer, an anti-angiogenesis agent, a cytokine, a molecular targeted drug, an immune checkpoint inhibitor or an oncolytic virus;

wherein, optionally, the method further comprises administering an additional antineoplastic therapy; and wherein, optionally, the method further comprises surgery or palliative therapy.

20. A method for detecting the presence or amount of of CLDN6 in a sample, comprising the steps of:

(1) contacting the sample with the antibody or antigen-binding fragment thereof according to claim 1;

(2) detecting the formation of a complex comprising the antibody or antigen-binding fragment thereof and CLDN6, or detecting an amount of the complex;

wherein, optionally, the CLDN6 is human CLDN6.

21. A method for determining whether a tumor is capable of being treated by an anti-tumor therapy targeting CLDN6, comprising the steps of:

(1) contacting a sample containing a cell of the tumor with an antibody or antigen-binding fragment thereof according to claim 1;

(2) detecting formation of a complex comprising the antibody or antigen-binding fragment thereof and the CLDN6;

wherein, optionally, the method is characterized by one or both of:

(1) the CLDN6 is human CLDN6; and (2) the tumor is selected from the group consisting of ovarian cancer, testicular cancer, gastric cancer, endometrial cancer, lung cancer, esophageal cancer, pancreatic cancer, bronchial cancer, breast cancer, ear nose throat (ENT) cancer, colon cancer, liver cancer, head and neck cancer, gallbladder cancer and metastasis thereof.

22. The method according to claim 19, wherein the tumor is selected from the group consisting of gastric cancer metastasis, Krukenberg tumor, peritoneal metastasis and lymph node metastasis.

23. The method according to claim 21, wherein the tumor is selected from the group consisting of gastric cancer metastasis, Krukenberg tumor, peritoneal metastasis and lymph node metastasis.

24. The method according to claim 19, wherein the method further comprises administering chemotherapy, radiation therapy, targeted therapy, immunotherapy, hormone therapy, or gene therapy.

* * * * *

SEQUENCE LISTING

```
<160> NUMBER OF SEQ ID NOS: 33

<210> SEQ ID NO 1
<211> LENGTH: 116
<212> TYPE: PRT
<213> ORGANISM: artificial
<220> FEATURE:
<223> OTHER INFORMATION: 15H2 heavy chain variable region

<400> SEQUENCE: 1

Asp Val Gln Leu Gln Glu Ser Gly Pro Gly Leu Val Lys Pro Ser Gln
```

```
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Phe Ser Ile Ile Arg Asp Thr Ser Lys Asn Gln Phe Phe
65                  70                  75                  80

Leu Lys Phe Asn Ser Val Thr Thr Glu Asp Thr Ala Thr Tyr Tyr Cys
                85                  90                  95

Ala Arg Gly Gly Tyr Tyr Phe Asp Tyr Trp Gly Gln Gly Thr Thr Leu
            100                 105                 110

Thr Val Ser Ser
        115


<210> SEQ ID NO 2
<211> LENGTH: 113
<212> TYPE: PRT
<213> ORGANISM: artificial
<220> FEATURE:
<223> OTHER INFORMATION: 15H2 light chain variable region

<400> SEQUENCE: 2

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Thr
            20                  25                  30

Asn Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Ala Pro Arg Thr Phe Gly Gly Gly Thr Lys Leu Glu Ile
            100                 105                 110

Lys


<210> SEQ ID NO 3
<211> LENGTH: 9
<212> TYPE: PRT
<213> ORGANISM: artificial
<220> FEATURE:
<223> OTHER INFORMATION: 15H2 HCDR1

<400> SEQUENCE: 3

Gly Tyr Ser Ile Thr Ser Gly Tyr Tyr
1               5


<210> SEQ ID NO 4
<211> LENGTH: 7
<212> TYPE: PRT
<213> ORGANISM: artificial
<220> FEATURE:
<223> OTHER INFORMATION: 15H2 HCDR2

<400> SEQUENCE: 4
```

Ile Ser Tyr Asp Gly Ser Asn
1 5

<210> SEQ ID NO 5
<211> LENGTH: 9
<212> TYPE: PRT
<213> ORGANISM: artificial
<220> FEATURE:
<223> OTHER INFORMATION: 15H2 HCDR3

<400> SEQUENCE: 5

Ala Arg Gly Gly Tyr Tyr Phe Asp Tyr
1 5

<210> SEQ ID NO 6
<211> LENGTH: 12
<212> TYPE: PRT
<213> ORGANISM: artificial
<220> FEATURE:
<223> OTHER INFORMATION: 15H2 LCDR1

<400> SEQUENCE: 6

Gln Ser Leu Leu Asn Thr Asn Asn Gln Lys Asn Tyr
1 5 10

<210> SEQ ID NO 7
<211> LENGTH: 7
<212> TYPE: PRT
<213> ORGANISM: artificial
<220> FEATURE:
<223> OTHER INFORMATION: 15H2 LCDR2

<400> SEQUENCE: 7

Phe Ala Ser Thr Arg Glu Ser
1 5

<210> SEQ ID NO 8
<211> LENGTH: 9
<212> TYPE: PRT
<213> ORGANISM: artificial
<220> FEATURE:
<223> OTHER INFORMATION: 15H2 LCDR3

<400> SEQUENCE: 8

Gln Gln His Tyr Asn Ala Pro Arg Thr
1 5

<210> SEQ ID NO 9
<211> LENGTH: 121
<212> TYPE: PRT
<213> ORGANISM: artificial
<220> FEATURE:
<223> OTHER INFORMATION: 7008-03 heavy chain variable region

<400> SEQUENCE: 9

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ile Tyr
20 25 30

Gly Met Ser Trp Val Arg Gln Ala Pro Gly Lys Gly Leu Glu Trp Val
35 40 45

Ala Thr Ile Ser Arg Asp Ala Ser Tyr Thr Tyr Phe Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Val Arg Leu Gly Asp Asn Asp Arg Gly Tyr Ala Met Asp Tyr Trp Gly
100 105 110

Gln Gly Thr Leu Val Thr Val Ser Ser
115 120

<210> SEQ ID NO 10
<211> LENGTH: 112
<212> TYPE: PRT
<213> ORGANISM: artificial
<220> FEATURE:
<223> OTHER INFORMATION: 7008-03 light chain variable region

<400> SEQUENCE: 10

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Val Val His Val
20 25 30

Asn Ala Asn Thr Tyr Leu Glu Trp Tyr Gln Gln Arg Pro Gly Gln Ser
35 40 45

Pro Arg Leu Leu Ile Tyr Lys Val Ser Asn Arg Phe Pro Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Arg Thr Phe Gly Gly Gly Thr Lys Val Glu Ile Lys
100 105 110

<210> SEQ ID NO 11
<211> LENGTH: 121
<212> TYPE: PRT
<213> ORGANISM: artificial
<220> FEATURE:
<223> OTHER INFORMATION: 9H3 heavy chain variable region

<400> SEQUENCE: 11

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Ser Ile Tyr
20 25 30

Gly Met Ser Trp Val Arg Gln Ser Pro Asp Arg Arg Leu Glu Trp Val
35 40 45

Ala Thr Ile Ser Arg Asp Gly Ser Tyr Thr Tyr Phe Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Val Arg Leu Gly Asp Asn Asp Arg Gly Tyr Ala Met Asp Tyr Trp Gly
100 105 110

Gln Gly Thr Ser Val Thr Val Ser Ser
115 120

<210> SEQ ID NO 12
<211> LENGTH: 112
<212> TYPE: PRT

<213> ORGANISM: artificial
<220> FEATURE:
<223> OTHER INFORMATION: 9H3 light chain variable region

<400> SEQUENCE: 12

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val His Val
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Asn Leu Glu Ile Lys
            100                 105                 110
```

<210> SEQ ID NO 13
<211> LENGTH: 8
<212> TYPE: PRT
<213> ORGANISM: artificial
<220> FEATURE:
<223> OTHER INFORMATION: 9H3 HCDR1

<400> SEQUENCE: 13

```
Gly Phe Thr Phe Ser Ile Tyr Gly
1               5
```

<210> SEQ ID NO 14
<211> LENGTH: 8
<212> TYPE: PRT
<213> ORGANISM: artificial
<220> FEATURE:
<223> OTHER INFORMATION: 9H3 HCDR2

<400> SEQUENCE: 14

```
Ile Ser Arg Asp Gly Ser Tyr Thr
1               5
```

<210> SEQ ID NO 15
<211> LENGTH: 14
<212> TYPE: PRT
<213> ORGANISM: artificial
<220> FEATURE:
<223> OTHER INFORMATION: 9H3 HCDR3

<400> SEQUENCE: 15

```
Val Arg Leu Gly Asp Asn Asp Arg Gly Tyr Ala Met Asp Tyr
1               5                   10
```

<210> SEQ ID NO 16
<211> LENGTH: 11
<212> TYPE: PRT
<213> ORGANISM: artificial
<220> FEATURE:
<223> OTHER INFORMATION: 9H3 LCDR1

<400> SEQUENCE: 16

```
Gln Ser Val Val His Val Asn Gly Asn Thr Tyr
1               5                   10
```

<210> SEQ ID NO 17
<211> LENGTH: 7
<212> TYPE: PRT
<213> ORGANISM: artificial
<220> FEATURE:
<223> OTHER INFORMATION: 9H3 LCDR2

<400> SEQUENCE: 17

```
Lys Val Ser Asn Arg Phe Pro
1               5
```

<210> SEQ ID NO 18
<211> LENGTH: 9
<212> TYPE: PRT
<213> ORGANISM: artificial
<220> FEATURE:
<223> OTHER INFORMATION: 9H3 LCDR3

<400> SEQUENCE: 18

```
Phe Gln Gly Ser His Val Pro Arg Thr
1               5
```

<210> SEQ ID NO 19
<211> LENGTH: 116
<212> TYPE: PRT
<213> ORGANISM: artificial
<220> FEATURE:
<223> OTHER INFORMATION: 7008-01 heavy chain variable region

<400> SEQUENCE: 19

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Pro Pro Gly Lys Gly Leu Glu Trp
        35                  40                  45

Met Gly Tyr Ile Ser Tyr Ser Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Tyr Phe Asp Tyr Trp Gly Gln Gly Thr Leu Val
            100                 105                 110

Thr Val Ser Ser
        115
```

<210> SEQ ID NO 20
<211> LENGTH: 113
<212> TYPE: PRT
<213> ORGANISM: artificial
<220> FEATURE:
<223> OTHER INFORMATION: 7008-01 light chain variable region

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Asn Asn Gln Lys Asn Tyr Leu Ala Trp Tyr Gln Gln Lys Pro Gly Gln
        35                  40                  45
```

-continued

```
Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Asn Ala Pro Arg Thr Phe Gly Gly Gly Thr Lys Val Glu Ile
            100                 105                 110

Lys


<210> SEQ ID NO 21
<211> LENGTH: 330
<212> TYPE: PRT
<213> ORGANISM: artificial
<220> FEATURE:
<223> OTHER INFORMATION: Human IgG1 heavy chain constant region

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 22
<211> LENGTH: 107
<212> TYPE: PRT
<213> ORGANISM: artificial
<220> FEATURE:
<223> OTHER INFORMATION: Human ?? light chain constant region

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 23
<211> LENGTH: 8
<212> TYPE: PRT
<213> ORGANISM: artificial
<220> FEATURE:
<223> OTHER INFORMATION: 7008-03 HCDR2

<400> SEQUENCE: 23

Ile Ser Arg Asp Ala Ser Tyr Thr
1               5


<210> SEQ ID NO 24
<211> LENGTH: 11
<212> TYPE: PRT
<213> ORGANISM: artificial
<220> FEATURE:
<223> OTHER INFORMATION: 7008-03 LCDR1

<400> SEQUENCE: 24

Gln Ser Val Val His Val Asn Ala Asn Thr Tyr
1               5                   10


<210> SEQ ID NO 25
<211> LENGTH: 348
<212> TYPE: DNA
<213> ORGANISM: artificial
<220> FEATURE:
<223> OTHER INFORMATION: Nucleic acid sequence encoding 15H2 heavy chain
      variable region

<400> SEQUENCE: 25

gatgtacagc ttcaggagtc aggacctggc ctcgtgaaac cttctcagtc tctgtctctc      60

acctgctctg tcactggcta ctccatcacc agtggttatt actggaactg gatccggcag     120
```

```
tttccaggaa acaaactgga atggatgggc tacataagct acgacggtag caataactac    180

aacccatctc tcaaaaatcg attctccatc attcgtgaca catctaagaa ccagtttttc    240

ctgaagttca attctgtgac tactgaggac acagctacat attactgcgc caggggggggg    300

tactactttg actactgggg ccaaggcacc actctcacag tctcctca                 348


<210> SEQ ID NO 26
<211> LENGTH: 339
<212> TYPE: DNA
<213> ORGANISM: artificial
<220> FEATURE:
<223> OTHER INFORMATION: Nucleic acid sequence encoding 15H2 light chain
      variable region

<400> SEQUENCE: 26

gacattgtga tgacacagtc tccatcctcc ctggctatgt cagtaggaca gaaggtcact     60

atgagctgca agtccagtca gagcctttta aatactaaca atcaaaagaa ctatttggcc    120

tggtaccagc agaaaccagg acagtctcct aaacttctgg tatactttgc atccactagg    180

gagtctgggg tccctgatcg cttcataggc agtggatctg ggacagattt cactcttacc    240

atcagcagtg tgcaggctga agacctggca gattacttct gtcaacaaca ttataacgct    300

cctcggacgt tcggtggagg caccaagctg gaaatcaaa                          339


<210> SEQ ID NO 27
<211> LENGTH: 363
<212> TYPE: DNA
<213> ORGANISM: artificial
<220> FEATURE:
<223> OTHER INFORMATION: Nucleic acid sequence encoding 9H3 heavy chain
      variable region

<400> SEQUENCE: 27

gaggtgcagc tggtggaatc tgggggagac ttagtgaagc ctggagggtc cctgaaactc     60

tcctgtgcag cctctggatt cactttcagt atctatggca tgtcttgggt tcgccagagt    120

ccagacagga ggctggaatg ggtcgcaacc attagtcgtg atggtagtta cacctacttt    180

ccagacagtg tgaaggggcg attcaccatc tccagagaca atgccaagaa caccctgtat    240

ttgcaaatga gcagtctgaa gtctgaggac acagccatgt attactgtgt aagactgggt    300

gataacgaca ggggctatgc tatggactac tggggtcaag gaacttcagt caccgtctcc    360

tca                                                                  363


<210> SEQ ID NO 28
<211> LENGTH: 336
<212> TYPE: DNA
<213> ORGANISM: artificial
<220> FEATURE:
<223> OTHER INFORMATION: Nucleic acid sequence encoding 9H3 light chain
      variable region

<400> SEQUENCE: 28

gatgttttga tgacccaaac tccactctcc ctgcctgtca gtcttggaga tcaagcctcc     60

atctcttgca gatctagtca gagtgttgta catgttaatg gaaacaccta tttagaatgg    120

tacctgcaga aaccaggcca gtctccaagg ctcctgatct acaaagtttc caaccgcttt    180

cctggggtcc cagacaggtt cagtggcagt ggatcaggga cagatttcac actcaggatc    240

agcagagtgg aggctgagga tctgggagtt tattactgct ttcaaggttc acatgttcct    300

cggacgttcg gtggaggcac caacctggaa atcaaa                              336
```

<210> SEQ ID NO 29
<211> LENGTH: 348
<212> TYPE: DNA
<213> ORGANISM: artificial
<220> FEATURE:
<223> OTHER INFORMATION: Nucleic acid sequence encoding 7008-01 heavy chain variable region

<400> SEQUENCE: 29
caggtgcagc tgcaggagag cggccccgga ctggtgaagc cctcagagac actgagcctg 60
acatgcacag tgagcggcta ctccattaca agcggctact actggaactg gatcagacag 120
ccccccggca agggcctgga atggatgggc tatatctcct acagcggcag caacaactac 180
aaccccagcc tgaagaacag ggtgaccatc tctcgcgaca cctccaagaa ccagttctcc 240
ctgaagctga gtagcgtgac tgccgctgac accgccgtgt actattgcgc cagaggcggc 300
tactacttcg actactgggg ccagggcacc ctggtgaccg tgagcagc 348

<210> SEQ ID NO 30
<211> LENGTH: 339
<212> TYPE: DNA
<213> ORGANISM: artificial
<220> FEATURE:
<223> OTHER INFORMATION: Nucleic acid sequence encoding 7008-01 light chain variable region

<400> SEQUENCE: 30
gacattgtga tgacccagag ccccgactcc ctggccgtga gcctgggaga aagagccacc 60
atcaactgca agagcagcca gagcctgctg aacaccaaca accagaaaaa ctacctggcc 120
tggtaccagc agaaacccgg ccagcccccc aaactgctga tctacttcgc ctccacccgc 180
gagtccggcg tgcctgatag attctccggc agcggcagcg gcaccgactt caccctgact 240
atcagcagcc tgcaggctga ggacgtggcc gtgtacttct gccagcagca ttacaacgct 300
cccagaacct ttggaggagg caccaaggtg gaaatcaag 339

<210> SEQ ID NO 31
<211> LENGTH: 363
<212> TYPE: DNA
<213> ORGANISM: artificial
<220> FEATURE:
<223> OTHER INFORMATION: Nucleic acid sequence encoding 7008-03 heavy chain variable region

<400> SEQUENCE: 31
gaggtgcagc tggtggagag cgggggggga ctggtgcagc caggaggaag cctgagactg 60
agctgtgccg ccagcgggtt tacatttagc atttatggga tgtcctgggt gagacaggcc 120
cccggaaaag gactggagtg ggtggctact atcagcagag acgctagcta cacctacttc 180
cccgattccg tgaagggcag attcacaatc agcagagata acgctaagaa cagcctgtat 240
ctgcagatga acagcctgcg ggccgaggac acagccgtgt attactgcgt gaggctgggc 300
gacaacgata gaggatacgc catggactac tgggggcagg gaacactggt gaccgtgagc 360
agc 363

<210> SEQ ID NO 32
<211> LENGTH: 336
<212> TYPE: DNA
<213> ORGANISM: artificial
<220> FEATURE:
<223> OTHER INFORMATION: Nucleic acid sequence encoding 7008-03 light -continued

```
      chain variable region

<400> SEQUENCE: 32

gacgtggtga tgacccagag cccccctgagc ctgcccgtga ccctgggaca gcccgctagt      60

atcagctgca gaagcagcca gagcgtggtg cacgtgaacg ccaacacata tctggagtgg     120

tatcagcaga ggcctggaca gagccccaga ctgctgatct acaaggtgag caacagattc     180

ccaggcgtgc cagacagatt ctctggaagc ggcagcggaa cagactttac cctgaagatc     240

tccagagtgg aggccgagga cgtgggagtg tactactgct tccagggcag ccacgtgccc     300

agaacattcg gcggcggcac caaagtggag atcaaa                               336


<210> SEQ ID NO 33
<211> LENGTH: 7
<212> TYPE: PRT
<213> ORGANISM: artificial
<220> FEATURE:
<223> OTHER INFORMATION: 7008-01 HCDR2

<400> SEQUENCE: 33

Ile Ser Tyr Ser Gly Ser Asn
1               5
```